(12) United States Patent
Zerkle et al.

(10) Patent No.: US 9,839,421 B2
(45) Date of Patent: Dec. 12, 2017

(54) JAW CLOSURE FEATURE FOR END EFFECTOR OF SURGICAL INSTRUMENT

(71) Applicant: Ethicon Endo-Surgery, Inc., Cincinnati, OH (US)

(72) Inventors: Jason E. Zerkle, Blanchester, OH (US); Robert J. Simms, Liberty Township, OH (US); Douglas B. Hoffman, Harrison, OH (US); Adam R. Dunki-Jacobs, Cincinnati, OH (US)

(73) Assignee: Ethicon LLC, Guaynabo, PR (US)

( * ) Notice: Subject to any disclaimer, the term of this patent is extended or adjusted under 35 U.S.C. 154(b) by 1004 days.

(21) Appl. No.: 13/780,120

(22) Filed: Feb. 28, 2013

(65) Prior Publication Data

US 2014/0239036 A1 Aug. 28, 2014

(51) Int. Cl.
*A61B 17/068* (2006.01)
*A61B 17/072* (2006.01)
*A61B 17/29* (2006.01)

(52) U.S. Cl.
CPC ...... *A61B 17/068* (2013.01); *A61B 17/07207* (2013.01); *A61B 2017/07257* (2013.01); *A61B 2017/2927* (2013.01); *A61B 2017/2933* (2013.01); *A61B 2017/2936* (2013.01)

(58) Field of Classification Search
CPC .. A61B 2017/07257; A61B 2017/2933; A61B 2017/2926
USPC ...................................................... 227/175.1
See application file for complete search history.

(56) References Cited

U.S. PATENT DOCUMENTS

| | | | |
|---|---|---|---|
| 4,805,823 A | 2/1989 | Rothfuss | |
| 5,415,334 A | 5/1995 | Williamson, IV et al. | |
| 5,452,837 A * | 9/1995 | Williamson, IV | A61B 17/07207 227/176.1 |
| 5,465,895 A | 11/1995 | Knodel et al. | |

(Continued)

FOREIGN PATENT DOCUMENTS

| | | |
|---|---|---|
| DE | 196 32 298 A1 | 2/1998 |
| EP | 0 829 235 A1 | 3/1998 |

(Continued)

OTHER PUBLICATIONS

U.S. Appl. No. 13/780,067, filed Feb. 28, 2013.

(Continued)

*Primary Examiner* — Thanh Truong
*Assistant Examiner* — Patrick Fry
(74) *Attorney, Agent, or Firm* — Frost Brown Todd LLC

(57) ABSTRACT

An end effector for use with a surgical instrument includes a first jaw, a second jaw, and a closure ring. The second jaw is pivotable relative to the first jaw. The second jaw has a proximal end with a first ramped surface and a second ramped surface distal of the first ramped surface. The closure ring is coupled with the second jaw to engage the first and second ramped surfaces of the second jaw. The closure ring translates from a proximal position to a distal position to engage the first ramped surface of the second jaw and then the second ramped surface of the second jaw. The camming engagement of the closure ring with the first and second ramped surfaces of the second jaw pivots the second jaw toward the first jaw. The closure ring may also provide camming engagement to pivot the second jaw away from the first jaw.

17 Claims, 24 Drawing Sheets

(56) References Cited

U.S. PATENT DOCUMENTS

| | | | |
|---|---|---|---|
| 5,597,107 A * | 1/1997 | Knodel | A61B 17/07207 227/175.2 |
| 5,632,432 A | 5/1997 | Schulze et al. | |
| 5,662,258 A | 9/1997 | Knodel et al. | |
| 5,662,667 A | 9/1997 | Knodel | |
| 5,673,840 A | 10/1997 | Schulze et al. | |
| 5,673,841 A | 10/1997 | Schulze et al. | |
| 5,704,534 A | 1/1998 | Huitema et al. | |
| 5,769,303 A | 6/1998 | Knodel et al. | |
| 5,792,135 A | 8/1998 | Madhani et al. | |
| 5,814,055 A * | 9/1998 | Knodel | A61B 17/07207 227/901 |
| 5,817,084 A | 10/1998 | Jensen | |
| 5,878,193 A | 3/1999 | Wang et al. | |
| 6,231,565 B1 | 5/2001 | Tovey et al. | |
| 6,364,888 B1 | 4/2002 | Niemeyer et al. | |
| 6,458,142 B1 | 10/2002 | Faller et al. | |
| 6,783,524 B2 | 8/2004 | Anderson et al. | |
| 6,786,382 B1 * | 9/2004 | Hoffman | A61B 17/07207 227/175.1 |
| 6,905,057 B2 | 6/2005 | Swayze et al. | |
| 6,959,852 B2 | 11/2005 | Shelton, IV et al. | |
| 6,978,921 B2 | 12/2005 | Shelton, IV et al. | |
| 7,000,818 B2 | 2/2006 | Shelton, IV et al. | |
| 7,044,352 B2 | 5/2006 | Shelton, IV et al. | |
| 7,083,075 B2 | 8/2006 | Swayze et al. | |
| 7,143,923 B2 | 12/2006 | Shelton, IV et al. | |
| 7,143,926 B2 | 12/2006 | Shelton, IV et al. | |
| 7,303,108 B2 | 12/2007 | Shelton, IV et al. | |
| 7,364,061 B2 | 4/2008 | Swayze et al. | |
| 7,367,485 B2 | 5/2008 | Shelton, IV et al. | |
| 7,380,695 B2 | 6/2008 | Doll et al. | |
| 7,380,696 B2 | 6/2008 | Shelton, IV et al. | |
| 7,404,508 B2 | 7/2008 | Smith et al. | |
| 7,434,715 B2 | 10/2008 | Shelton, IV et al. | |
| 7,524,320 B2 | 4/2009 | Tierney et al. | |
| 7,644,848 B2 | 1/2010 | Swayze et al. | |
| 7,691,098 B2 | 4/2010 | Wallace et al. | |
| 7,721,930 B2 | 5/2010 | McKenna et al. | |
| 7,726,537 B2 * | 6/2010 | Olson | A61B 17/07207 227/175.1 |
| 7,806,891 B2 | 10/2010 | Nowlin et al. | |
| 8,210,411 B2 | 7/2012 | Yates et al. | |
| 8,215,531 B2 | 7/2012 | Shelton, IV et al. | |
| 8,408,439 B2 | 4/2013 | Huang et al. | |
| 8,453,914 B2 | 6/2013 | Laurent et al. | |
| 8,479,969 B2 | 7/2013 | Shelton, IV et al. | |
| 8,573,461 B2 | 11/2013 | Shelton, IV et al. | |
| 8,573,465 B2 | 11/2013 | Shelton, IV | |
| 8,602,288 B2 | 12/2013 | Shelton, IV et al. | |
| 8,616,431 B2 | 12/2013 | Timm et al. | |
| 2006/0180634 A1 | 8/2006 | Shelton, IV et al. | |
| 2007/0010838 A1 | 1/2007 | Shelton, IV et al. | |
| 2007/0084897 A1 | 4/2007 | Shelton, IV et al. | |
| 2007/0175955 A1 | 8/2007 | Shelton, IV et al. | |
| 2010/0063527 A1 * | 3/2010 | Beaupre | A61B 17/320092 606/169 |
| 2011/0278343 A1 * | 11/2011 | Knodel | A61B 17/07207 227/176.1 |
| 2012/0138660 A1 | 6/2012 | Shelton, IV et al. | |
| 2012/0199630 A1 | 8/2012 | Shelton, IV et al. | |
| 2012/0199632 A1 | 8/2012 | Spivey et al. | |
| 2012/0203247 A1 | 8/2012 | Shelton, IV et al. | |
| 2013/0012957 A1 | 1/2013 | Shelton, IV et al. | |
| 2015/0374361 A1 * | 12/2015 | Gettinger | A61B 17/068 227/175.2 |

FOREIGN PATENT DOCUMENTS

| | | |
|---|---|---|
| EP | 2 324 778 A2 | 5/2011 |
| WO | WO 2004/032763 A2 | 4/2004 |
| WO | WO 2010/088044 A2 | 8/2010 |

OTHER PUBLICATIONS

U.S. Appl. No. 13/780,082, filed Feb. 28, 2013.
U.S. Appl. No. 13/780,106, filed Feb. 28, 2013.
U.S. Appl. No. 13/780,379, filed Feb. 28, 2013.
U.S. Appl. No. 13/780,402, filed Feb. 28, 2013.
U.S. Appl. No. 13/780,417, filed Feb. 28, 2013.
Partial European Search Report dated Jun. 16, 2014 for Application No. EP 14157370.9, 8 pgs.
European Search Report and Written Opinion dated Oct. 21, 2014 for Application No. EP 14157370.9, 12 pgs.
International Search Report dated Nov. 18, 2014 for Application No. PCT/US2014/016208, 10 pgs.
International Preliminary Report on Patentability and Written Opinion dated Sep. 1, 2015 for Application No. PCT/US2014/016208, 12 pgs.

* cited by examiner

JAW CLOSURE FEATURE FOR END EFFECTOR OF SURGICAL INSTRUMENT

BACKGROUND

In some settings, endoscopic surgical instruments may be preferred over traditional open surgical devices since a smaller incision may reduce the post-operative recovery time and complications. Consequently, some endoscopic surgical instruments may be suitable for placement of a distal end effector at a desired surgical site through the cannula of a trocar. These distal end effectors may engage tissue in a number of ways to achieve a diagnostic or therapeutic effect (e.g., endocutter, grasper, cutter, stapler, clip applier, access device, drug/gene therapy delivery device, and energy delivery device using ultrasound, RF, laser, etc.). Endoscopic surgical instruments may include a shaft between the end effector and a handle portion, which is manipulated by the clinician. Such a shaft may enable insertion to a desired depth and rotation about the longitudinal axis of the shaft, thereby facilitating positioning of the end effector within the patient. Positioning of an end effector may be further facilitated through inclusion of one or more articulation joints or features, enabling the end effector to be selectively articulated or otherwise deflected relative to the longitudinal axis of the shaft.

Examples of endoscopic surgical instruments include surgical staplers. Some such staplers are operable to clamp down on layers of tissue, cut through the clamped layers of tissue, and drive staples through the layers of tissue to substantially seal the severed layers of tissue together near the severed ends of the tissue layers. Merely exemplary surgical staplers are disclosed in U.S. Pat. No. 4,805,823, entitled "Pocket Configuration for Internal Organ Staplers," issued Feb. 21, 1989; U.S. Pat. No. 5,415,334, entitled "Surgical Stapler and Staple Cartridge," issued May 16, 1995; U.S. Pat. No. 5,465,895, entitled "Surgical Stapler Instrument," issued Nov. 14, 1995; U.S. Pat. No. 5,597,107, entitled "Surgical Stapler Instrument," issued Jan. 28, 1997; U.S. Pat. No. 5,632,432, entitled "Surgical Instrument," issued May 27, 1997; U.S. Pat. No. 5,673,840, entitled "Surgical Instrument," issued Oct. 7, 1997; U.S. Pat. No. 5,704,534, entitled "Articulation Assembly for Surgical Instruments," issued Jan. 6, 1998; U.S. Pat. No. 5,814,055, entitled "Surgical Clamping Mechanism," issued Sep. 29, 1998; U.S. Pat. No. 6,978,921, entitled "Surgical Stapling Instrument Incorporating an E-Beam Firing Mechanism," issued Dec. 27, 2005; U.S. Pat. No. 7,000,818, entitled "Surgical Stapling Instrument Having Separate Distinct Closing and Firing Systems," issued Feb. 21, 2006; U.S. Pat. No. 7,143,923, entitled "Surgical Stapling Instrument Having a Firing Lockout for an Unclosed Anvil," issued Dec. 5, 2006; U.S. Pat. No. 7,303,108, entitled "Surgical Stapling Instrument Incorporating a Multi-Stroke Firing Mechanism with a Flexible Rack," issued Dec. 4, 2007; U.S. Pat. No. 7,367,485, entitled "Surgical Stapling Instrument Incorporating a Multistroke Firing Mechanism Having a Rotary Transmission," issued May 6, 2008; U.S. Pat. No. 7,380,695, entitled "Surgical Stapling Instrument Having a Single Lockout Mechanism for Prevention of Firing," issued Jun. 3, 2008; U.S. Pat. No. 7,380,696, entitled "Articulating Surgical Stapling Instrument Incorporating a Two-Piece E-Beam Firing Mechanism," issued Jun. 3, 2008; U.S. Pat. No. 7,404,508, entitled "Surgical Stapling and Cutting Device," issued Jul. 29, 2008; U.S. Pat. No. 7,434,715, entitled "Surgical Stapling Instrument Having Multistroke Firing with Opening Lockout," issued Oct. 14, 2008; U.S. Pat. No. 7,721,930, entitled "Disposable Cartridge with Adhesive for Use with a Stapling Device," issued May 25, 2010; U.S. Pub. No. 2010/0264193, entitled "Surgical Stapling Instrument with An Articulatable End Effector," published Oct. 21, 2010, now U.S. Pat. No. 8,408,439, issued on Apr. 2, 2013; and U.S. Pub. No. 2012/0239012, entitled "Motor-Driven Surgical Cutting Instrument with Electric Actuator Directional Control Assembly," published Sep. 20, 2012, now U.S. Pat. No. 8,453,914, issued on Jun. 4, 2013. The disclosure of each of the above-cited U.S. patents and U.S. patent Publications is incorporated by reference herein.

While the surgical staplers referred to above are described as being used in endoscopic procedures, it should be understood that such surgical staplers may also be used in open procedures and/or other non-endoscopic procedures. By way of example only, a surgical stapler may be inserted through a thoracotomy and thereby between a patient's ribs to reach one or more organs in a thoracic surgical procedure that does not use a trocar as a conduit for the stapler. Such procedures may include the use of the stapler to sever and close a vessel leading to a lung. For instance, the vessels leading to an organ may be severed and closed by a stapler before removal of the organ from the thoracic cavity. Of course, surgical staplers may be used in various other settings and procedures.

While various kinds of surgical stapling instruments and associated components have been made and used, it is believed that no one prior to the inventor(s) has made or used the invention described in the appended claims.

BRIEF DESCRIPTION OF THE DRAWINGS

The accompanying drawings, which are incorporated in and constitute a part of this specification, illustrate embodiments of the invention, and, together with the general description of the invention given above, and the detailed description of the embodiments given below, serve to explain the principles of the present invention.

Figure 1:
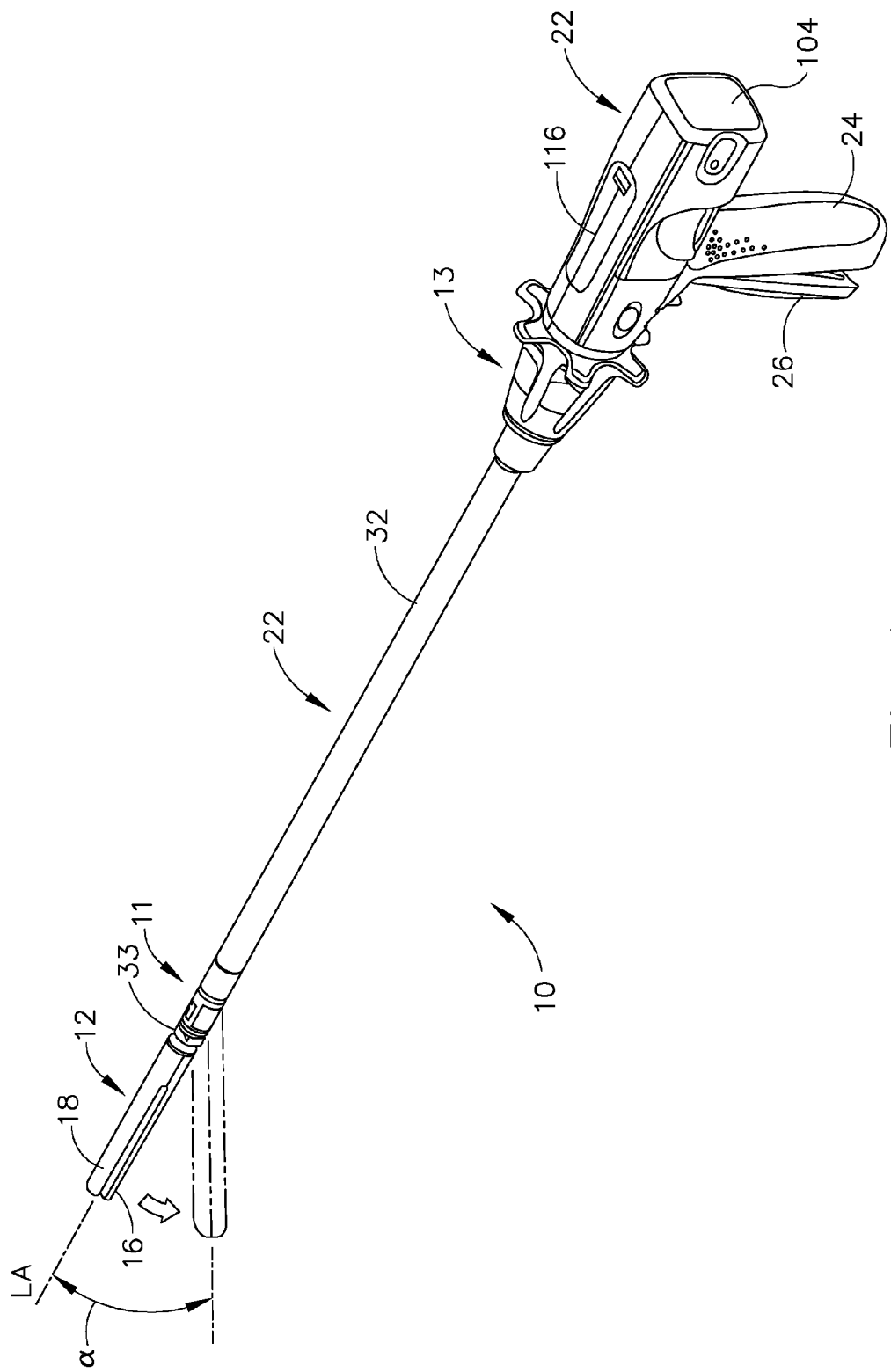
FIG. 1 depicts a perspective view of an exemplary articulating surgical stapling instrument.
Figure 2:
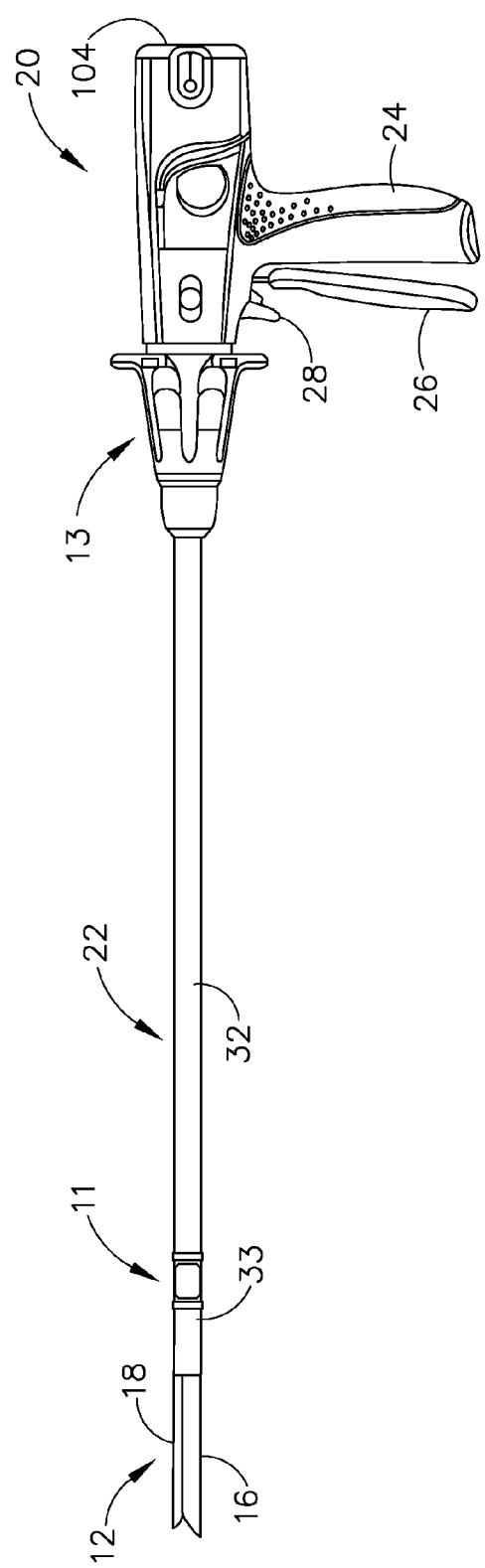
FIG. 2 depicts a side elevational view of the instrument of FIG. 1.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

I. Exemplary Surgical Stapler

FIGS. 1-7 depict an exemplary surgical stapling and severing instrument (10) that is sized for insertion, in a nonarticulated state as depicted in FIG. 1, through a trocar cannula to a surgical site in a patient for performing a surgical procedure. By way of example only, such a trocar may be inserted in a patient's abdomen, between two of the patient's ribs, or elsewhere. In some settings, instrument (10) is used without a trocar. For instance, instrument (10) may be inserted directly through a thoracotomy or other type of incision. Instrument (10) of the present example includes a handle portion (20) connected to a shaft (22). Shaft (22) distally terminates in an articulation joint (11), which is further coupled with an end effector (12). It should be understood that terms such as "proximal" and "distal" are used herein with reference to a clinician gripping handle portion (20) of instrument (10). Thus, end effector (12) is distal with respect to the more proximal handle portion (20). It will be further appreciated that for convenience and clarity, spatial terms such as "vertical" and "horizontal" are used herein with respect to the drawings. However, surgical instruments are used in many orientations and positions, and these terms are not intended to be limiting and absolute.

In some versions, shaft (22) is constructed in accordance with at least some of the teachings of U.S. patent application Ser. No. 13/780,402, entitled "Surgical Instrument with Multi-Diameter Shaft," filed on Feb. 28, 2013, published as U.S. Pub. No. 2014/0239038 on Aug. 28, 2014, the disclosure of which is incorporated by reference herein. Other suitable configurations for shaft (22) will be apparent to those of ordinary skill in the art in view of the teachings herein.

Once articulation joint (11) and end effector (12) are inserted through the cannula passageway of a trocar, articulation joint (11) may be remotely articulated, as depicted in phantom in FIG. 1, by an articulation control (13), such that end effector (12) may be deflected from the longitudinal axis (LA) of shaft (22) at a desired angle ($\alpha$). End effector (12) may thereby reach behind an organ or approach tissue from a desired angle or for other reasons. In some versions, articulation joint (11) enables deflection of end effector (12) along a single plane. In some other versions, articulation joint (11) enables deflection of end effector along more than one plane. Articulation joint (11) and articulation control (13) may be configured in accordance with the teachings of any of the numerous references that are cited herein. Alternatively, articulation joint (11) and/or articulation control (13) may have any other suitable configuration. By way of example only, articulation control (13) may instead be configured as a knob that rotates about an axis that is perpendicular to the longitudinal axis (LA) of shaft (22).

In some versions, articulation joint (11) and/or articulation control (13) are/is constructed and operable in accordance with at least some of the teachings of U.S. patent application Ser. No. 13/780,067, entitled "Surgical Instrument End Effector Articulation Drive with Pinion and Opposing Racks," filed on Feb. 28, 2013, now U.S. Pat. No. 9,189,142, issued on Nov. 17, 2015, the disclosure of which is incorporated by reference herein. Articulation joint (11) may also be constructed and operable in accordance with at least some of the teachings of U.S. patent application Ser. No. 13/780,402, filed on Feb. 28, 2013, published as U.S. Pub. No. 2014/0239038 on Aug. 28, 2014, the disclosure of which is incorporated by reference herein. Other suitable forms that articulation joint (11) and articulation control (13) may take will be apparent to those of ordinary skill in the art in view of the teachings herein.

End effector (12) of the present example includes a lower jaw (16) and a pivotable anvil (18). In some versions, lower jaw (16) is constructed in accordance with at least some of the teachings of U.S. patent application Ser. No. 13/780,417, entitled "Installation Features for Surgical Instrument End Effector Cartridge," filed on Feb. 28, 2013, published as U.S. Pub. No. 2014/0239044 on Aug. 28, 2014, the disclosure of which is incorporated by reference herein. Various exemplary features, configurations, and operabilities that may be incorporated into anvil (18) will be described in greater detail below. In addition, anvil (18) may be constructed in accordance with at least some of the teachings of U.S. patent application Ser. No. 13/780,106, entitled "Integrated Tissue Positioning and Jaw Alignment Features for Surgical Stapler," filed on Feb. 28, 2013, now U.S. Pat. No. 9,517,065, issued on Dec. 13, 2016, the disclosure of which is incorporated by reference herein; and/or at least some of the teachings of U.S. patent application Ser. No. 13/780,379, entitled "Staple Forming Features for Surgical Stapling Instrument," filed on Feb. 28, 2013, published as U.S. Pub. No. 2014/0239037 on Aug. 28, 2014, the disclosure of which is incorporated by reference herein. Other suitable forms that lower jaw (16) and anvil (18) may take will be apparent to those of ordinary skill in the art in view of the teachings herein.

Handle portion (20) includes a pistol grip (24) and a closure trigger (26). Closure trigger (26) is pivotable toward pistol grip (24) to cause clamping, or closing, of the anvil (18) toward lower jaw (16) of end effector (12). Such closing of anvil (18) is provided through a closure tube (32) and a closure ring (33), which both longitudinally translate relative to handle portion (20) in response to pivoting of closure trigger (26) relative to pistol grip (24). Closure tube (32) extends along the length of shaft (22); and closure ring (33) is positioned distal to articulation joint (11). Articulation joint (11) is operable to communicate/transmit longitudinal movement from closure tube (32) to closure ring (33).

Handle portion (20) also includes a firing trigger (28). An elongate member (136) (shown in FIG. 11) longitudinally extends through shaft (22) and communicates a longitudinal firing motion from handle portion (20) to a firing beam (14) in response to actuation of firing trigger (28). This distal translation of firing beam (14) causes the stapling and severing of clamped tissue in end effector (12), as will be described in greater detail below. Thereafter, triggers (26, 28) may be released to release the tissue from end effector (12).

FIGS. 3-6 depict end effector (12) employing an E-beam form of firing beam (14) to perform a number of functions. It should be understood that an E-beam form is just a merely illustrative example. Firing beam (14) may take any other suitable form, including but not limited to non-E-beam forms. As best seen in FIGS. 4A-4B, firing beam (14) includes a transversely oriented upper pin (38), a firing beam cap (44), a transversely oriented middle pin (46), and a distally presented cutting edge (48). Upper pin (38) is positioned and translatable within a longitudinal anvil slot (42) of anvil (18). Firing beam cap (44) slidably engages a lower surface of lower jaw (16) by having firing beam (14) extend through lower jaw slot (45) (shown in FIG. 4B) that is formed through lower jaw (16). Middle pin (46) slidingly engages a top surface of lower jaw (16), cooperating with firing beam cap (44). Thereby, firing beam (14) affirmatively spaces end effector (12) during firing.

Some non-E-beam forms of firing beam (14) may lack upper pin (38), middle pin (46) and/or firing beam cap (44). Some such versions of instrument (10) may simply rely on closure ring (33) or some other feature to pivot anvil (18) to a closed position and hold anvil (18) in the closed position while firing beam (14) advances to the distal position. By way of example only, firing beam (14) and/or associated lockout features may be constructed and operable in accordance with at least some of the teachings of U.S. patent application Ser. No. 13/780,082, entitled "Lockout Feature for Movable Cutting Member of Surgical Instrument," filed on Feb. 28, 2013, now U.S. Pat. No. 9,717,497, issued on Aug. 1, 2017, the disclosure of which is incorporated by reference herein. Other suitable forms that firing beam (14) may take will be apparent to those of ordinary skill in the art in view of the teachings herein.

Figure 3:
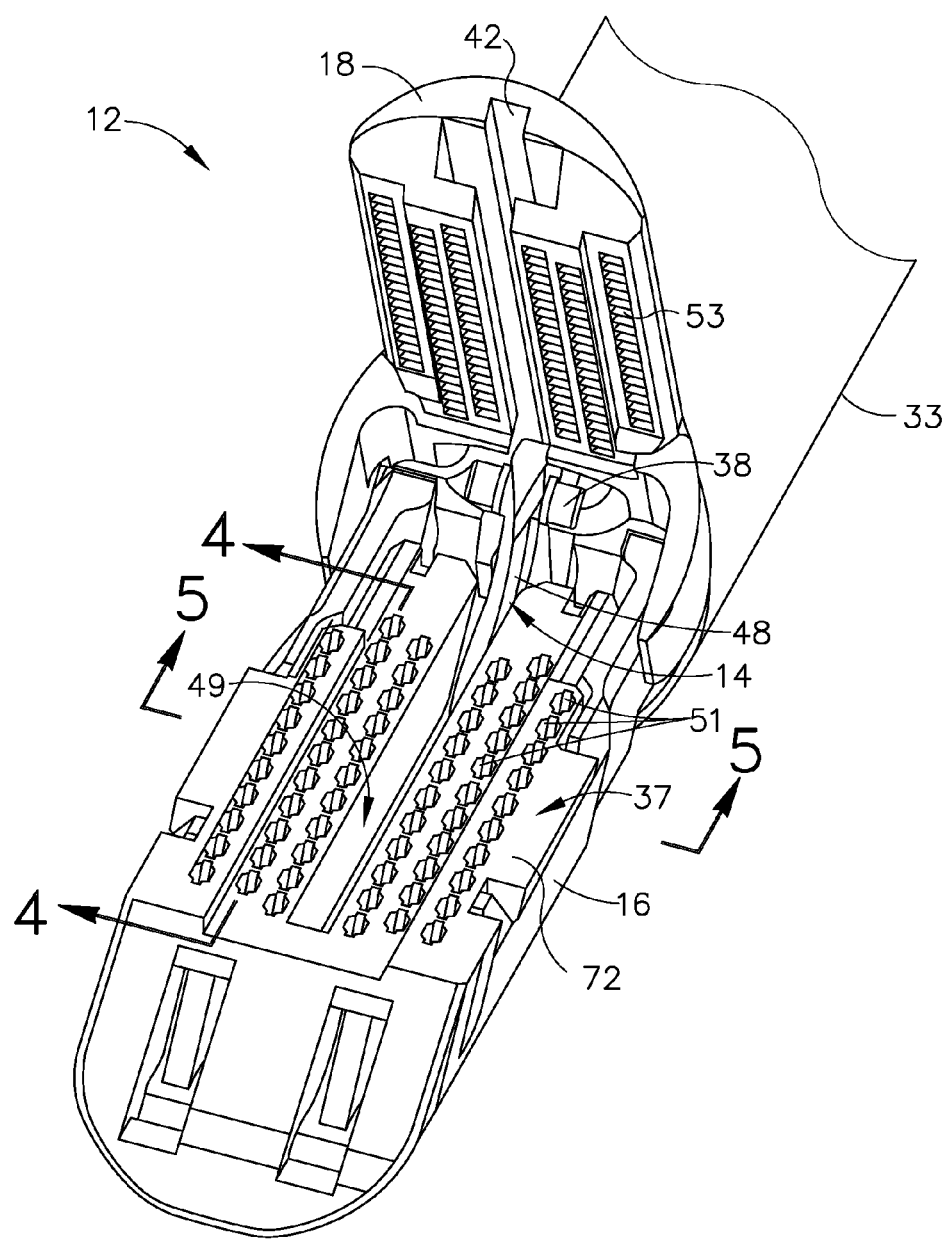
FIG. 3 depicts a perspective view of an opened end effector of the instrument of FIG. 1.
Figure 4A:
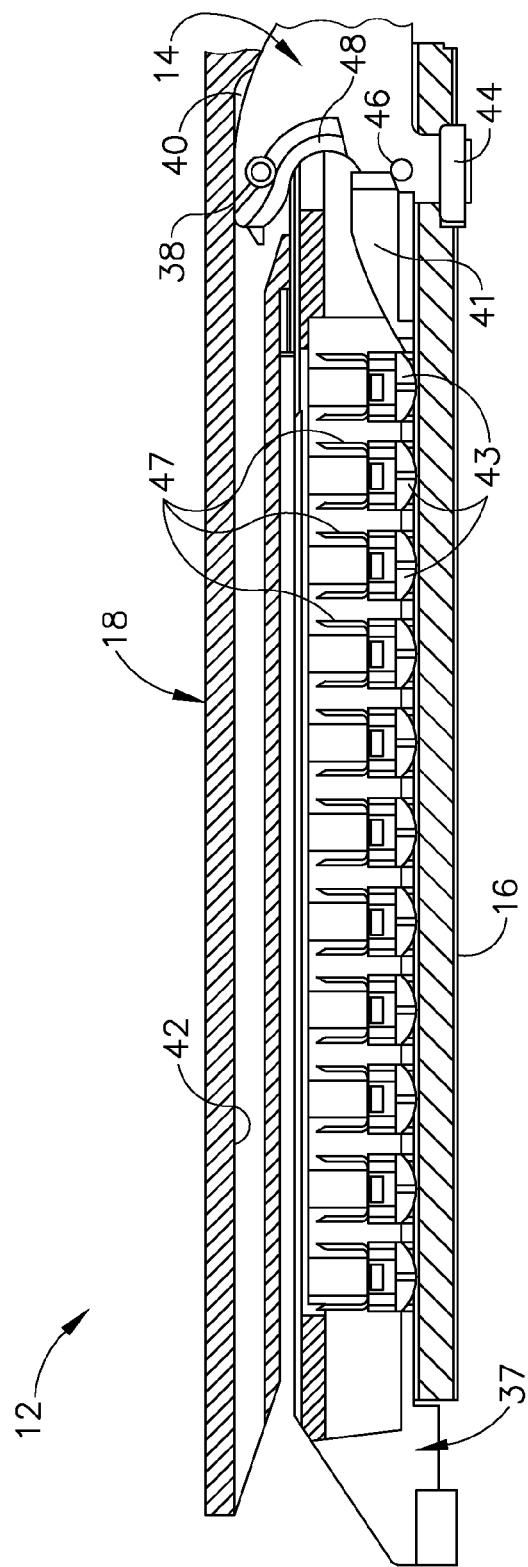
FIG. 4A depicts a side cross-sectional view of the end effector of FIG. 3, taken along line 4-4 of FIG. 3, with the firing beam in a proximal position.
Figure 4B:
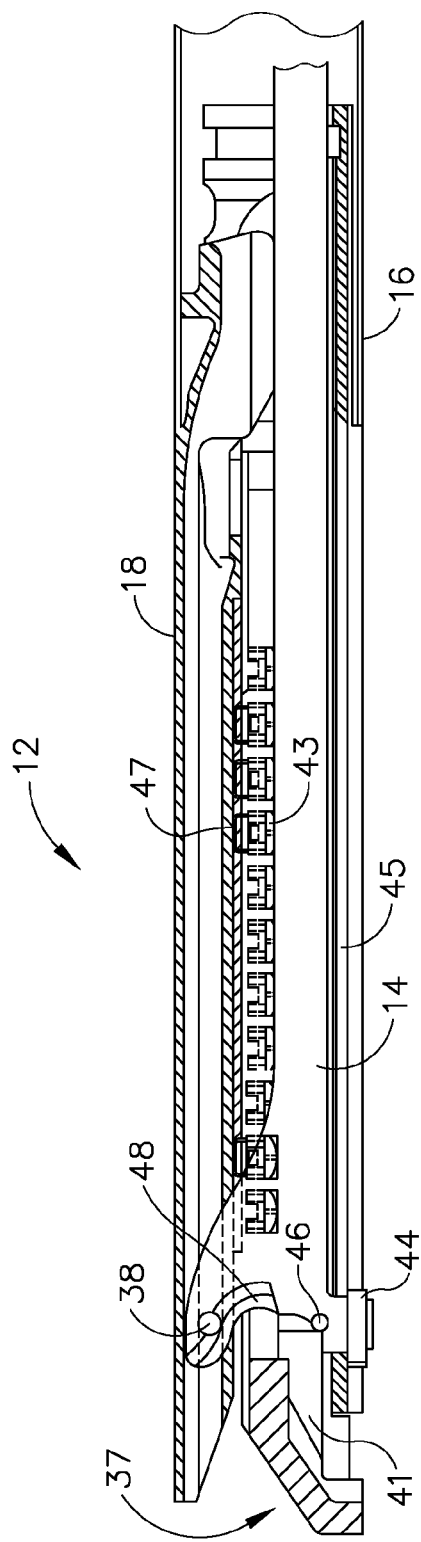
FIG. 4B depicts a side cross-sectional view of the end effector of FIG. 3, taken along line 4-4 of FIG. 3, with the firing beam in a distal position.
Figure 5:
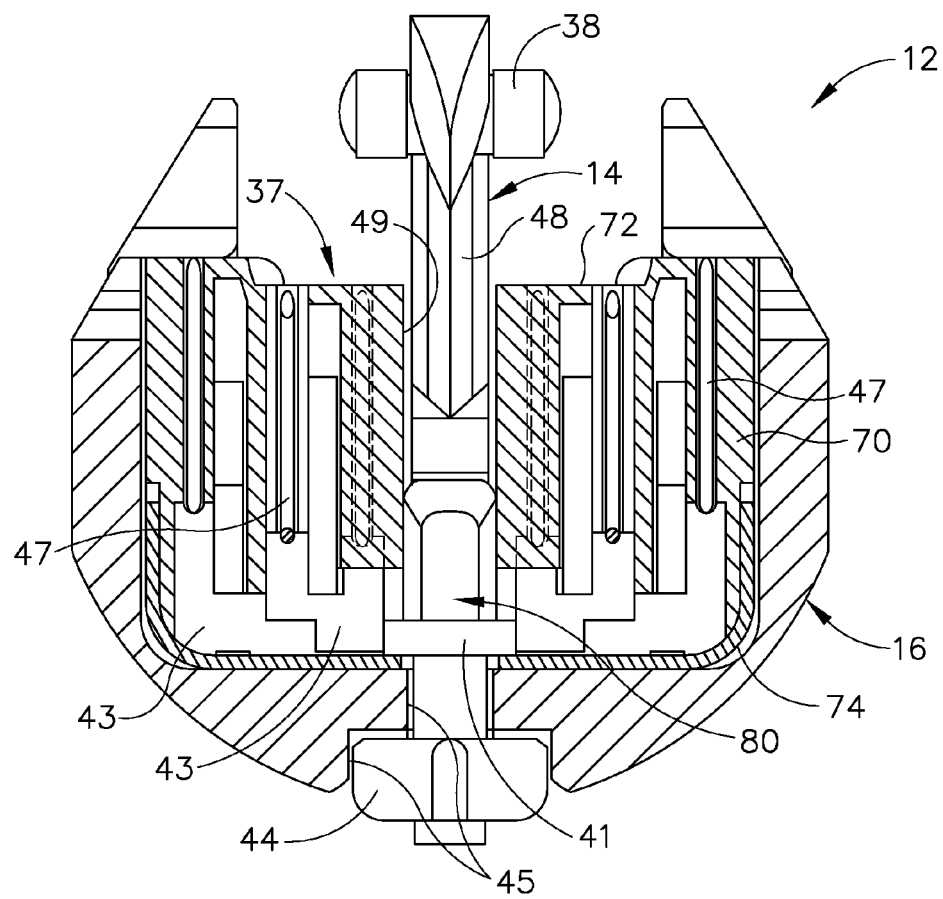
FIG. 5 depicts an end cross-sectional view of the end effector of FIG. 3, taken along line 5-5 of FIG. 3.
Figure 6:
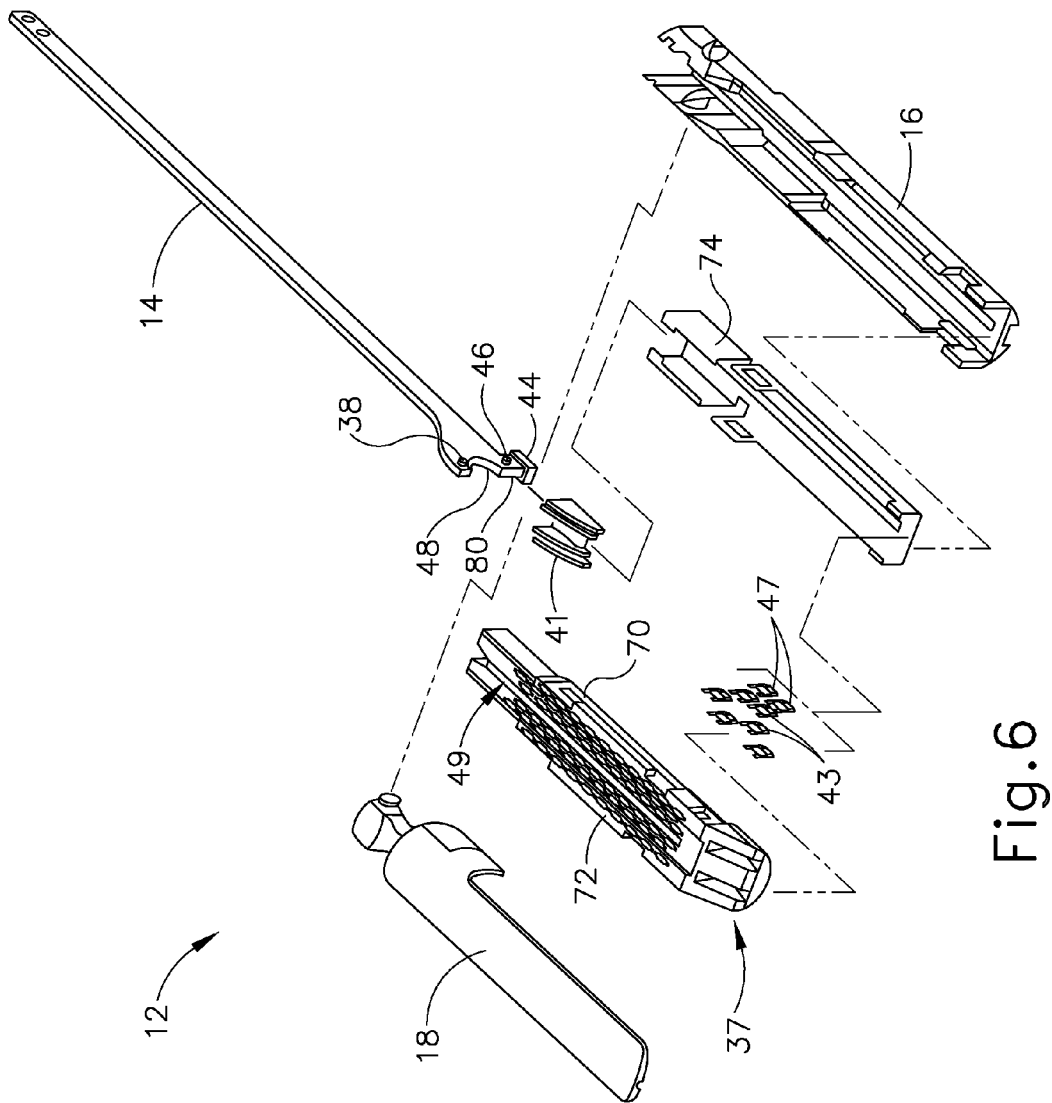
FIG. 6 depicts an exploded perspective view of the end effector of FIG. 3.

FIG. 3 shows firing beam (14) of the present example proximally positioned and anvil (18) pivoted to an open position, allowing an unspent staple cartridge (37) to be removably installed into a channel of lower jaw (16). As best seen in FIGS. 5-6, staple cartridge (37) of this example includes a cartridge body (70), which presents an upper deck (72) and is coupled with a lower cartridge tray (74). As best seen in FIG. 3, a vertical slot (49) is formed through part of staple cartridge (37). As also best seen in FIG. 3, three rows of staple apertures (51) are formed through upper deck (72) on one side of vertical slot (49), with another set of three rows of staple apertures (51) being formed through upper deck (72) on the other side of vertical slot (49). Of course, any other suitable number of staple rows (e.g., two rows, four rows, any other number) may be provided. Referring back to FIGS. 4A-6, a wedge sled (41) and a plurality of staple drivers (43) are captured between cartridge body (70) and tray (74), with wedge sled (41) being located proximal to staple drivers (43). Wedge sled (41) is movable longitudinally within staple cartridge (37); while staple drivers (43) are movable vertically within staple cartridge (37). Staples (47) are also positioned within cartridge body (70), above corresponding staple drivers (43). In particular, each staple (47) is driven vertically within cartridge body (70) by a staple driver (43) to drive staple (47) out through an associated staple aperture (51). As best seen in FIGS. 4A-4B and 6, wedge sled (41) presents inclined cam surfaces that urge staple drivers (43) upwardly as wedge sled (41) is driven distally through staple cartridge (37).

In some versions, staple cartridge (37) is constructed and operable in accordance with at least some of the teachings of U.S. patent application Ser. No. 13/780,106, filed on Feb. 28, 2013, now U.S. Pat. No. 9,517,065, issued on Dec. 13, 2016, the disclosure of which is incorporated by reference herein. In addition or in the alternative, staple cartridge (37) may be constructed and operable in accordance with at least some of the teachings of U.S. patent application Ser. No. 13/780,417, filed on Feb. 28, 2013, published as U.S. Pub. No. 2014/0239044 on Aug. 28, 2014, the disclosure of which is incorporated by reference herein. Other suitable forms that staple cartridge (37) may take will be apparent to those of ordinary skill in the art in view of the teachings herein.

With end effector (12) closed as depicted in FIGS. 4A-4B by distally advancing closure tube (32) and closure ring (33), firing beam (14) is then advanced in engagement with anvil (18) by having upper pin (38) enter longitudinal anvil slot (42). A pusher block (80) (shown in FIG. 5) is located at the distal end of firing beam (14), and is configured to engage wedge sled (41) such that wedge sled (41) is pushed distally by pusher block (80) as firing beam (14) is advanced distally through staple cartridge (37) when firing trigger (28) is actuated. During such firing, cutting edge (48) of firing beam (14) enters vertical slot (49) of staple cartridge (37), severing tissue clamped between staple cartridge (37) and anvil (18). As shown in FIGS. 4A-4B, middle pin (46) and pusher block (80) together actuate staple cartridge (37) by entering into vertical slot (49) within staple cartridge (37), driving wedge sled (41) into upward camming contact with staple drivers (43) that in turn drive staples (47) out through staple apertures (51) and into forming contact with staple forming pockets (53) (shown in FIG. 3) on the inner surface of anvil (18). FIG. 4B depicts firing beam (14) fully distally translated after completing severing and stapling of tissue. It should be understood that staple forming pockets (53) are intentionally omitted from the view in FIGS. 4A-4B; but staple forming pockets (53) are shown in FIG. 3. It should also be understood that anvil (18) is intentionally omitted from the view in FIG. 5.

Figure 7:
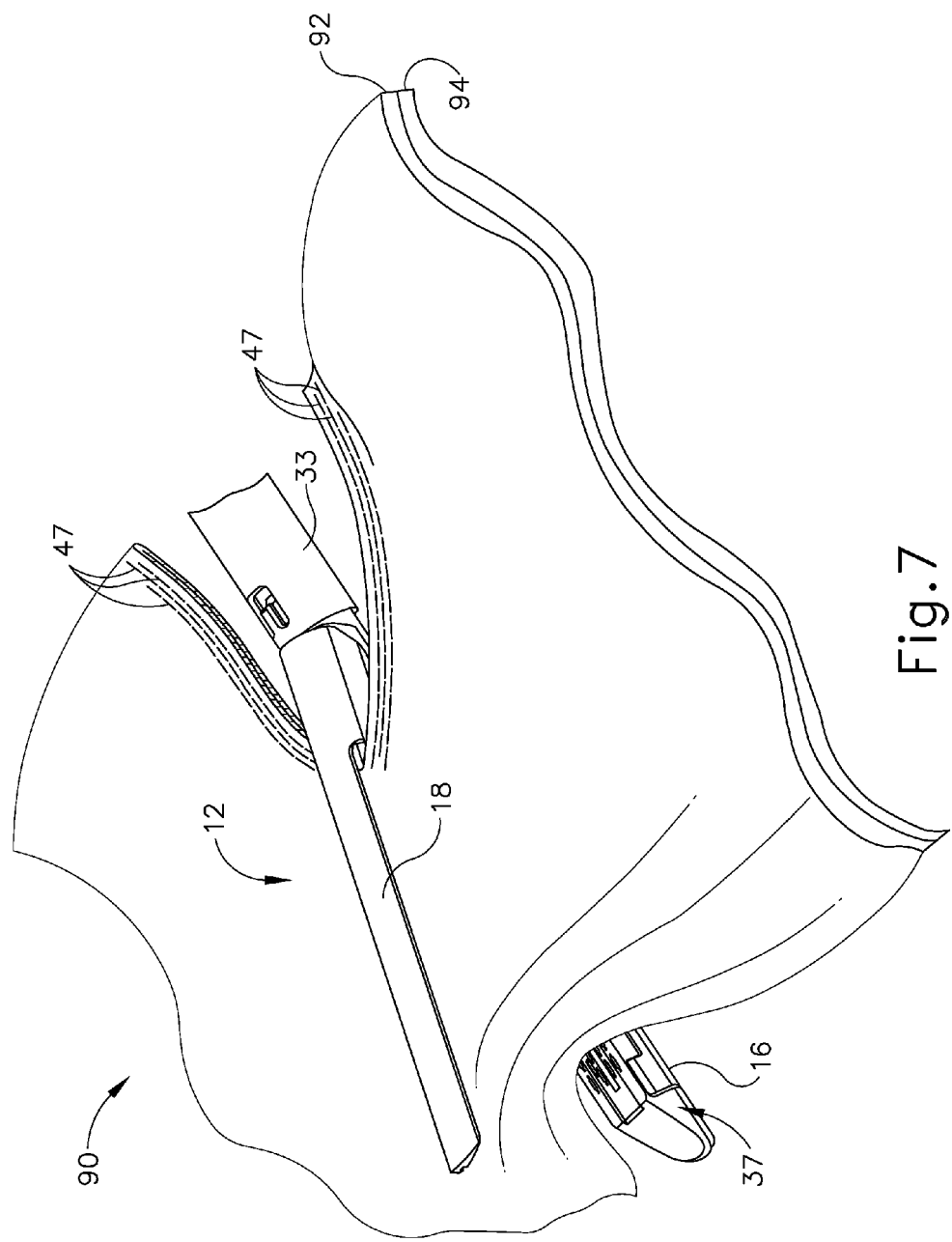
FIG. 7 depicts a perspective view of the end effector of FIG. 3, positioned at tissue and having been actuated once in the tissue.

FIG. 7 shows end effector (12) having been actuated through a single stroke through tissue (90). As shown, cutting edge (48) (obscured in FIG. 7) has cut through tissue (90), while staple drivers (43) have driven three alternating rows of staples (47) through the tissue (90) on each side of the cut line produced by cutting edge (48). Staples (47) are all oriented substantially parallel to the cut line in this example, though it should be understood that staples (47) may be positioned at any suitable orientations. In the present example, end effector (12) is withdrawn from the trocar after the first stroke is complete, spent staple cartridge (37) is replaced with a new staple cartridge, and end effector (12) is then again inserted through the trocar to reach the stapling site for further cutting and stapling. This process may be repeated until the desired amount of cuts and staples (47) have been provided. Anvil (18) may need to be closed to facilitate insertion and withdrawal through the trocar; and anvil (18) may need to be opened to facilitate replacement of staple cartridge (37).

It should be understood that cutting edge (48) may sever tissue substantially contemporaneously with staples (47) being driven through tissue during each actuation stroke. In the present example, cutting edge (48) just slightly lags behind driving of staples (47), such that a staple (47) is driven through the tissue just before cutting edge (48) passes through the same region of tissue, though it should be understood that this order may be reversed or that cutting edge (48) may be directly synchronized with adjacent staples. While FIG. 7 shows end effector (12) being actuated in two layers (92, 94) of tissue (90), it should be understood that end effector (12) may be actuated through a single layer of tissue (90) or more than two layers (92, 94) of tissue. It should also be understood that the formation and positioning of staples (47) adjacent to the cut line produced by cutting edge (48) may substantially seal the tissue at the cut line, thereby reducing or preventing bleeding and/or leaking of other bodily fluids at the cut line. Furthermore, while FIG. 7 shows end effector (12) being actuated in two substantially flat, apposed planar layers (92, 94) of tissue, it should be understood that end effector (12) may also be actuated across a tubular structure such as a blood vessel, a section of the gastrointestinal tract, etc. FIG. 7 should therefore not be viewed as demonstrating any limitation on the contemplated uses for end effector (12). Various suitable settings and procedures in which instrument (10) may be used will be apparent to those of ordinary skill in the art in view of the teachings herein.

It should be understood that instrument (10) may be configured and operable in accordance with any of the teachings of U.S. Pat. No. 4,805,823; U.S. Pat. No. 5,415,334; U.S. Pat. No. 5,465,895; U.S. Pat. No. 5,597,107; U.S. Pat. No. 5,632,432; U.S. Pat. No. 5,673,840; U.S. Pat. No. 5,704,534; U.S. Pat. No. 5,814,055; U.S. Pat. No. 6,978,921; U.S. Pat. No. 7,000,818; U.S. Pat. No. 7,143,923; U.S. Pat. No. 7,303,108; U.S. Pat. No. 7,367,485; U.S. Pat. No. 7,380,695; U.S. Pat. No. 7,380,696; U.S. Pat. No. 7,404,508; U.S. Pat. No. 7,434,715; U.S. Pat. No. 7,721,930; U.S. Pub. No. 2010/0264193, now U.S. Pat. No. 8,408,439; and/or 2012/0239012, now U.S. Pat. No. 8,453,914. As noted above, the disclosures of each of those patents and publications are incorporated by reference herein. Additional exemplary modifications that may be provided for instrument (10) will be described in greater detail below. Various suitable ways in which the below teachings may be incorporated into instrument (10) will be apparent to those of ordinary skill in the art. Similarly, various suitable ways in which the below teachings may be combined with various teachings of the patents/publications cited herein will be apparent to those of ordinary skill in the art. It should also be understood that the below teachings are not limited to instrument (10) or devices taught in the patents cited herein. The below teachings may be readily applied to various other kinds of instruments, including instruments that would not be classified as surgical staplers. Various other suitable devices and settings in which the below teachings may be applied will be apparent to those of ordinary skill in the art in view of the teachings herein.

II. Exemplary Motorized Drive Features

Figure 8:
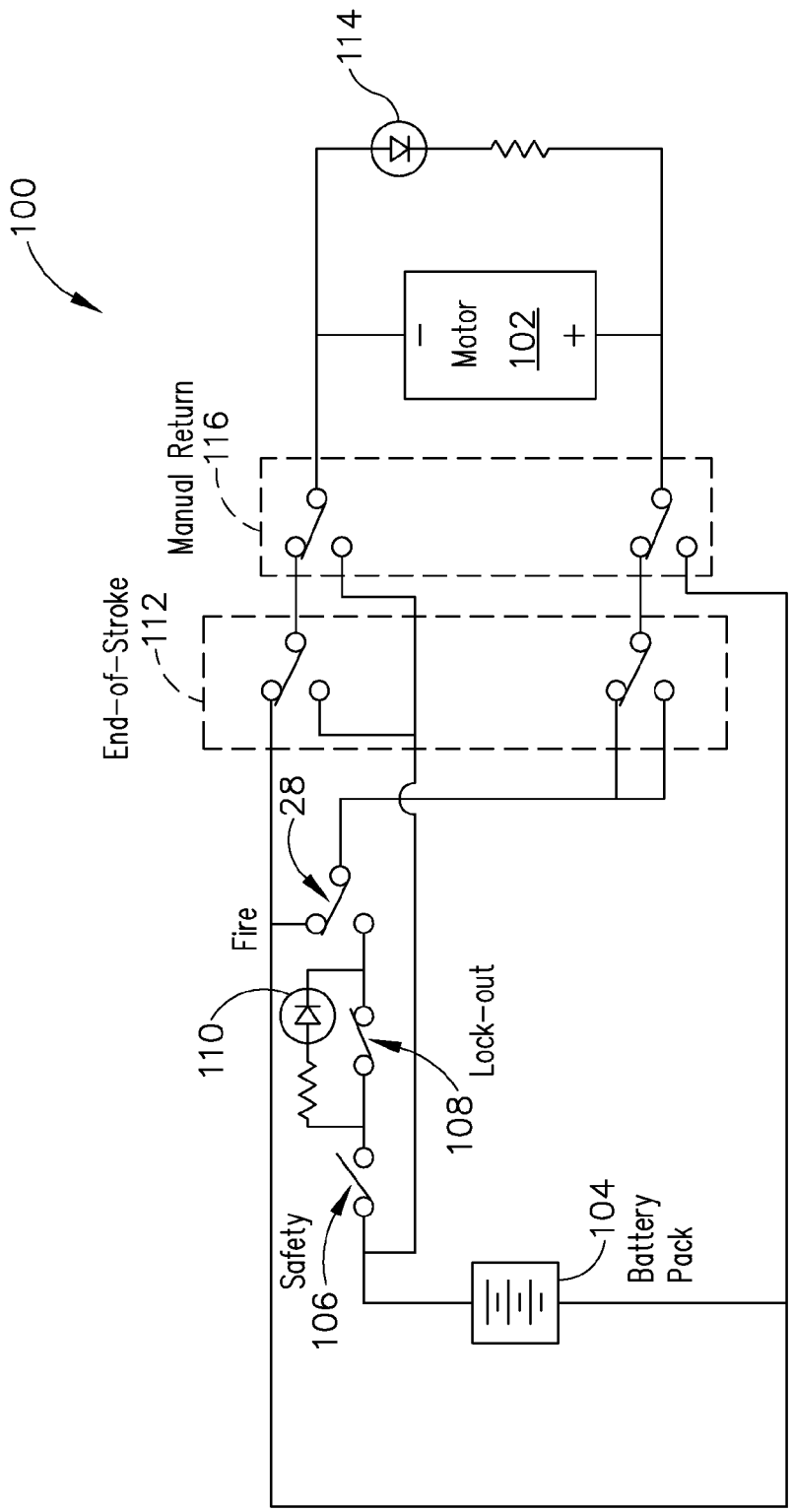
FIG. 8 depicts a schematic view of an exemplary control circuit for use in the instrument of FIG. 1.

In the present example, instrument (10) provides motorized control of firing beam (14). FIGS. 8-11 show exemplary components that may be used to provide motorized control of firing beam (14). In particular, FIG. 8 shows an exemplary control circuit (100) that may be used to power an electric motor (102) with electric power from a battery pack (104) (also shown in FIGS. 1-2). Electric motor (102) is operable to translate firing beam (14) longitudinally as will be described in greater detail below. It should be understood that the entire control circuit (100), including motor (102) and battery pack (104), may be housed within handle portion (20). FIG. 8 shows firing trigger (28) as an open switch, though it should be understood that this switch is closed when firing trigger (28) is actuated. Circuit (100) of this example also includes a safety switch (106) that must be closed in order to complete circuit (100), though it should be understood that safety switch (106) is merely optional. Safety switch (106) may be closed by actuating a separate button, slider, or other feature on handle portion (20).

Circuit (100) of the present example also includes a lockout switch (108), which is configured to be closed by default but is automatically opened in response to a lockout condition. By way of example only, a lockout condition may include one or more of the following: the absence of a cartridge (37) in lower jaw (16), the presence of a spent (e.g., previously fired) cartridge (37) in lower jaw (16), an insufficiently closed anvil (18), a determination that instrument (10) has been fired too many times, and/or any other suitable conditions. Various sensors, algorithms, and other features that may be used to detect lockout conditions will be apparent to those of ordinary skill in the art in view of the teachings herein. Similarly, other suitable kinds of lockout conditions will be apparent to those of ordinary skill in the art in view of the teachings herein. It should be understood that circuit (100) is opened and thus motor (102) is inoperable when lockout switch (108) is opened. A lockout indicator (110) (e.g., an LED, etc.) is operable to provide a visual indication of the status of lockout switch (108). By way of example only, lockout switch (108), lockout indicator (110), and associated components/functionality may be configured in accordance with at least some of the teachings of U.S. Pat. No. 7,644,848, entitled "Electronic Lockouts and Surgical Instrument Including Same," issued Jan. 12, 2010, the disclosure of which is incorporated by reference herein.

Once firing beam (14) reaches a distal-most position (e.g., at the end of a cutting stroke), an end-of-stroke switch (112) is automatically switched to a closed position, reversing the polarity of the voltage applied to motor (102). This reverses the direction of rotation of motor (102), it being understood that the operator will have released firing trigger (28) at this stage of operation. In this operational state, current flows through a reverse direction indicator (114) (e.g., an LED, etc.) to provide a visual indication to the operator that motor (102) rotation has been reversed. Various suitable ways in which end-of-stroke switch (112) may be automatically switched to a closed position when firing beam (14) reaches a distal-most position will be apparent to those of ordinary skill in the art in view of the teachings herein. Similarly, various suitable forms that reverse direction indicator (114) may take will be apparent to those of ordinary skill in the art in view of the teachings herein.

Handle portion (20) of the present example also includes a manual return switch (116), which is also shown in circuit (100). Manual return switch (116) is configured to act as a "bailout" feature, enabling the operator to quickly begin retracting firing beam (14) proximally during a firing stroke. In other words, manual return switch (116) may be manually actuated when firing beam (14) has only been partially advanced distally. Manual return switch (116) may provide functionality similar to end-of-stroke switch (112), reversing the polarity of the voltage applied to motor (102) to thereby reverse the direction of rotation of motor (102). Again, this reversal may be visually indicated through reverse direction indicator (114).

In some versions, one or more of switches (28, 106, 108, 112, 116) are in the form of microswitches. Other suitable forms will be apparent to those of ordinary skill in the art in view of the teachings herein. In addition to or in lieu of the foregoing, at least part of circuit (100) may be configured in accordance with at least some of the teachings of U.S. Pat. No. 8,210,411, entitled "Motor-Driven Surgical Instrument," issued Jul. 3, 2012, the disclosure of which is incorporated by reference herein.

Figure 9:
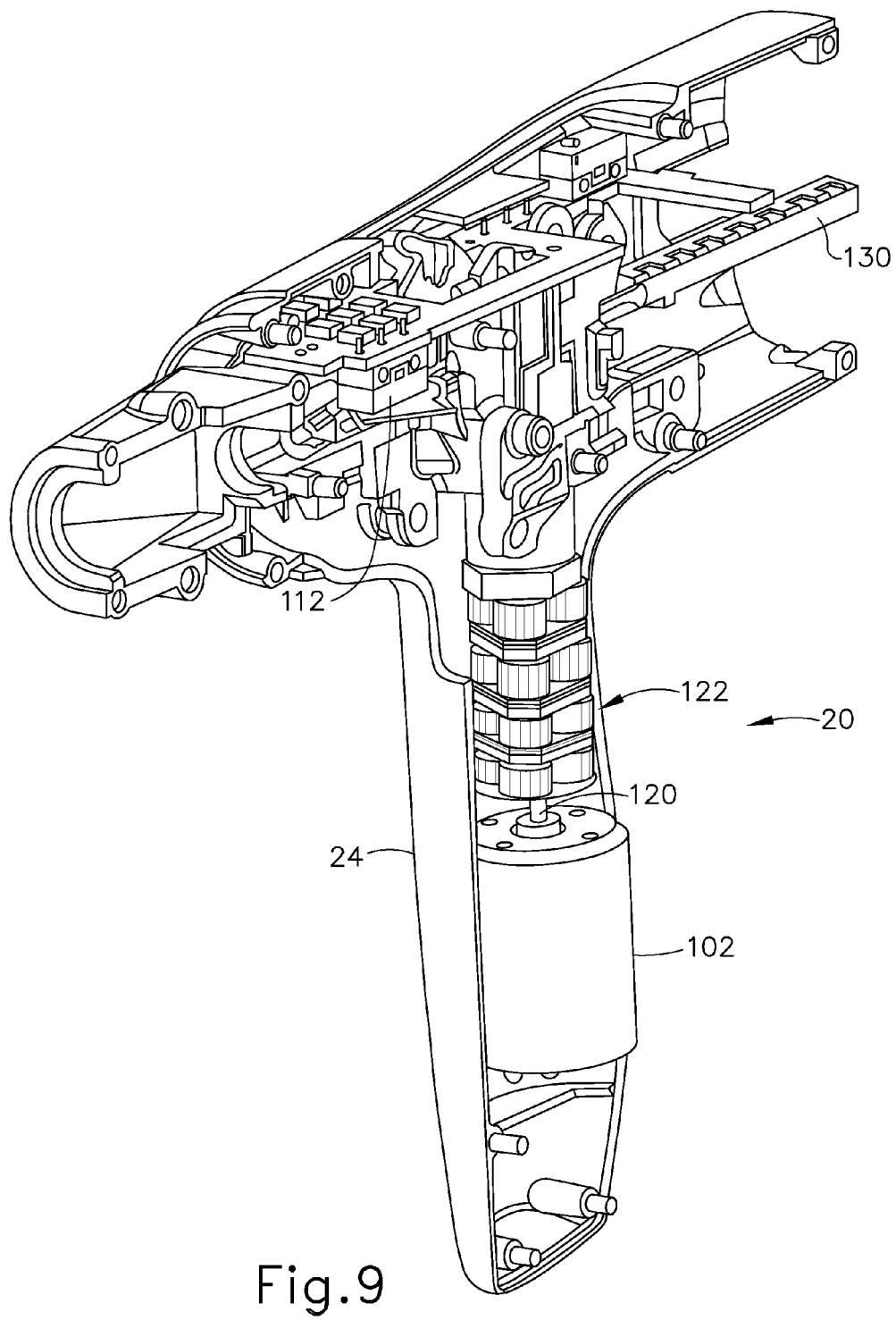
FIG. 9 depicts a perspective view of the handle assembly of the instrument of FIG. 1, with a housing half removed.
Figure 10:
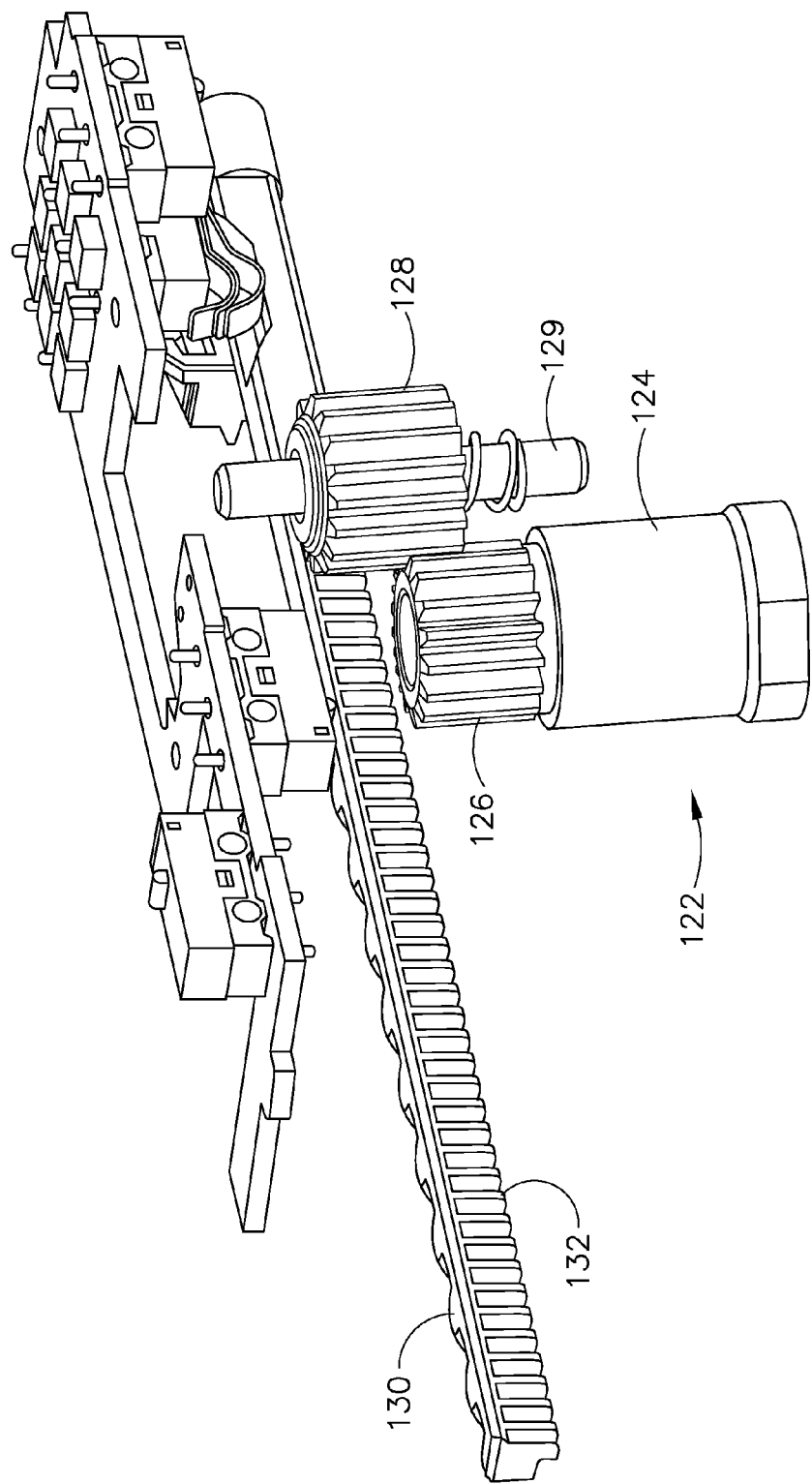
FIG. 10 depicts a perspective view of drive assembly components from the handle assembly of FIG. 9.
Figure 11:
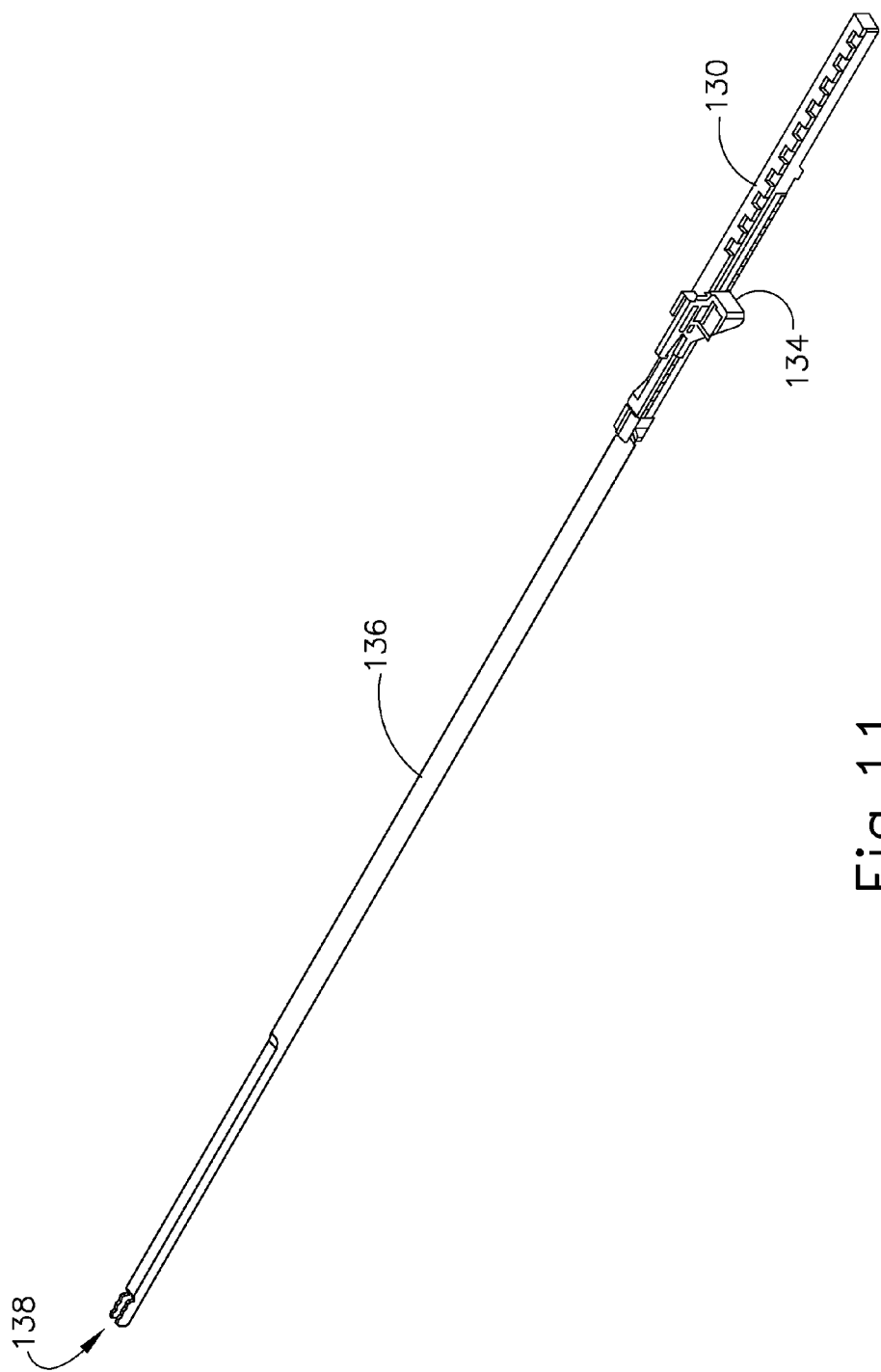
FIG. 11 depicts a perspective view of an elongate member from the drive assembly of FIG. 10.

FIGS. 9-11 show various mechanical components that may be used to provide motorized translation of firing beam (14). In particular, FIG. 9 shows motor (102) housed in pistol grip (24) of handle portion (20). It should be understood that battery pack (104) (shown in FIGS. 1-2) may also be located in pistol grip (24) (e.g., below motor (102)) and/or elsewhere within handle portion (20). Motor (102) has a drive shaft (120) that is coupled with a gear assembly (122). Gear assembly (122) has an external casing (not shown) and is operable to drive an upper gear (126), which is shown in FIG. 10. Upper gear (126) meshes with a pinion (128), which is rotatably supported by a pin (129) secured in handle portion (20). It should therefore be understood that activation of motor (102) will ultimately rotate pinion (128) within handle portion (20).

As also shown in FIGS. 9-10, a translating rack (130) includes teeth (132) that mesh with pinion (128), such that rack (130) translates longitudinally when pinion (128) rotates. As shown in FIG. 11, rack (130) is coupled with an elongate member (136), which extends through shaft (22) and includes a distal end (138) that couples with the proximal end of firing beam (14). Elongate member (136) translates within shaft (22), such that elongate member (136) communicates longitudinal motion of rack (130) to firing beam (14). It should therefore be understood that activation of motor (102) will ultimately translate firing beam (14) within end effector (12). In particular, motor (102) may drive firing beam (14) distally to sever tissue (90) and drive staples (47) into tissue (90). A switch actuation arm (134) extends laterally from rack (130), and is positioned to engage end-of-stroke switch (112) when firing beam (14) reaches a distal-most position (e.g., after tissue (90) has been severed and staples (47) have been driven into tissue (90)). As noted above, this engagement of end-of-stroke switch (112) automatically reverses motor (102) to return firing beam (14) from the distal-most position to the proximal position, enabling anvil (18) to be pivoted away from lower jaw (16) to release tissue (90).

Use of the term "pivot" (and similar terms with "pivot" as a base) should not be read as necessarily requiring pivotal movement about a fixed axis. In some versions, anvil (18) pivots about an axis that is defined by a pin (or similar feature) that slides along an elongate slot or channel as anvil (18) moves toward lower jaw (16). In such versions, the pivot axis translates along the path defined by the slot or channel while anvil (18) simultaneously pivots about that axis. In addition or in the alternative, the pivot axis may slide along the slot/channel first, with anvil (18) then pivoting about the pivot axis after the pivot axis has slid a certain distance along the slot/channel. It should be understood that such sliding/translating pivotal movement is encompassed within terms such as "pivot," "pivots," "pivotal," "pivotable," "pivoting," and the like. Of course, some versions may provide pivotal movement of anvil (18) about an axis that remains fixed and does not translate within a slot or channel, etc.

In addition to or in lieu of the foregoing, the features operable to drive firing beam (14) may be configured in accordance with at least some of the teachings of U.S. Pub. No. 2012/0239012, now U.S. Pat. No. 8,453,914, the disclosure of which is incorporated by reference herein; and/or in accordance with at least some of the teachings of U.S. Pub. No. 2012/0239012, now U.S. Pat. No. 8,453,914, the disclosure of which is also incorporated by reference herein. Other suitable components, features, and configurations for providing motorization of firing beam (14) will be apparent to those of ordinary skill in the art in view of the teachings herein. It should also be understood that some other versions may provide manual driving of firing beam (14), such that a motor may be omitted. By way of example only, firing beam (14) may be actuated in accordance with at least some of the teachings of any other patent/publication reference cited herein.

III. Exemplary End Effector Engagement Features

In some instances, it may be desirable to increase the mechanical load capability of end effector (12) during closure. For example, increased mechanical load capability may be desired for stapling thick or dense tissue. The increased mechanical load capability may also decrease or account for inadvertent movement between jaws (16, 18). Accordingly, ramp engagement features may be provided on end effector (12) to increase the mechanical load capability. The examples below include several merely illustrative versions of ramp engagement features that may be readily introduced to an end effector (12).

A. Exemplary Ramp Engagement Features

Figure 12:
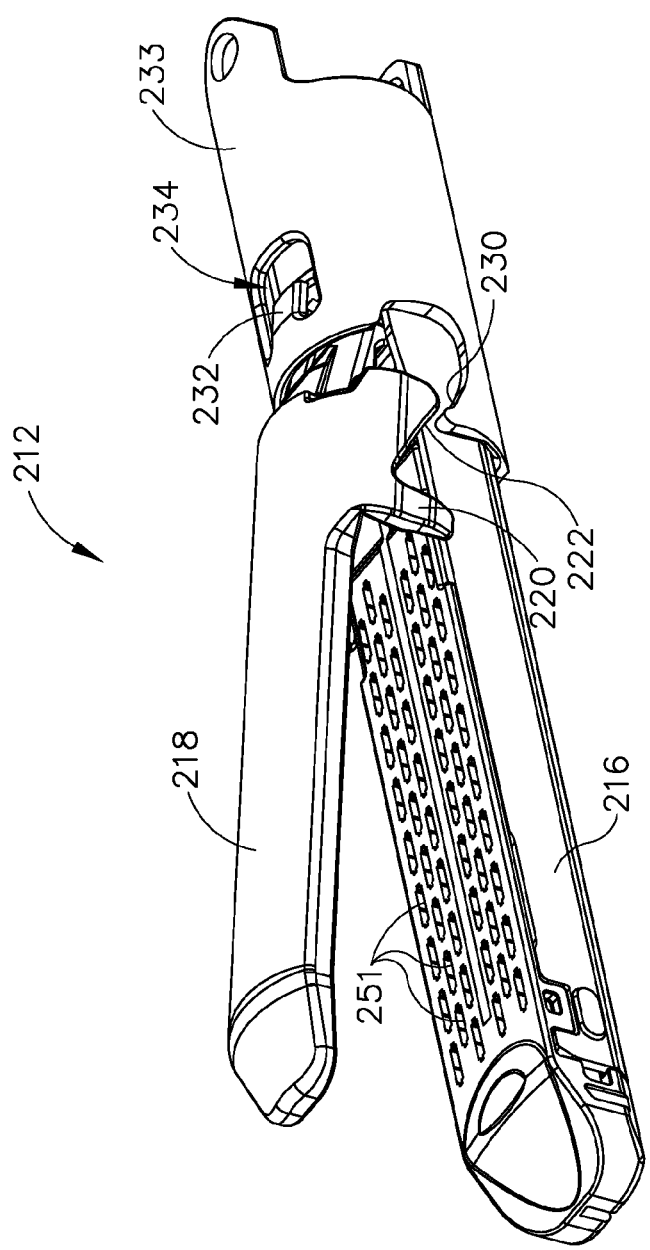
FIG. 12 depicts a perspective view of another exemplary end effector for use with the instrument of FIG. 1.

FIG. 12 shows an exemplary end effector (212) that may be readily incorporated into instrument (10). End effector (212) comprises a lower jaw (216), a pivotable anvil (218), and a closure ring (233). Lower jaw (216) is similar to lower jaw (16) of end effector (12). Pivotable anvil (218) is similar to pivotable anvil (18), except that pivotable anvil (218) comprises ramp engagement features that correspond with closure ring (233) to increase the mechanical load capability of end effector (212). Closure ring (233) of end effector (212) is similar to closure ring (33), except that closure ring (233) comprises extensions (230).

Figure 13:
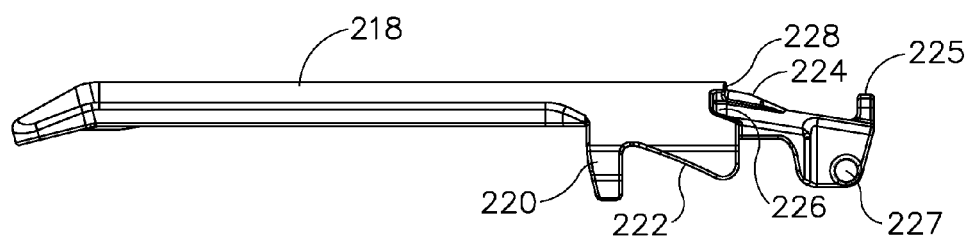
FIG. 13 depicts a side elevational view of a pivoting jaw of the end effector of FIG. 12.
Figure 14:
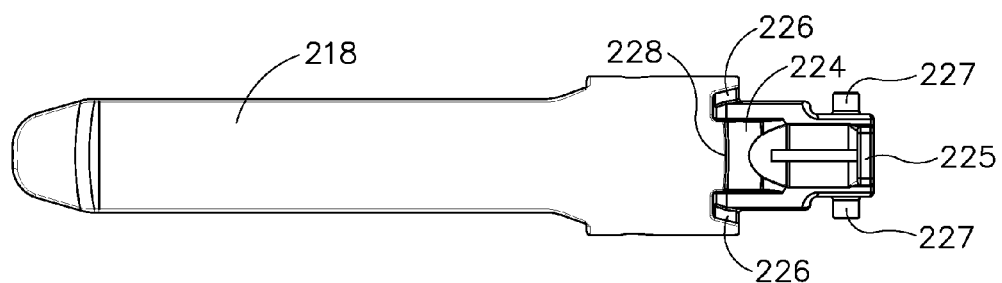
FIG. 14 depicts a top plan view of the pivoting jaw of FIG. 13.

FIGS. 13-14 show pivotable anvil (218) in more detail. Pivotable anvil (218) comprises a central ramp (224), upper side ramps (226), and extensions (220). Central ramp (224) is positioned centrally on the top surface of a proximal portion of anvil (218). Central ramp (224) slopes downwardly in the proximal direction. A vertical surface (228) extends upwardly from a distal end of central ramp (224). As shown in FIG. 14, vertical surface (228) has a curved profile. Side ramps (226) are positioned on either side of central ramp (224). Similar to central ramp (224), side ramps (226) slope downwardly in the proximal direction, but side ramps (226) do not extend as far proximally as central ramp (224). A tab (225) extends upwardly from the proximal end of central ramp (224). Pins (227) extend outwardly from the proximal end of anvil (218) to engage lower jaw (216) such that anvil (218) is pivotable relative to lower jaw (216). While pins (227) of the present example pivot, pins (227) do not pivot about a fixed axis. Instead, pins (227) slide relative to lower jaw (216) in addition to pivoting, such that the pivot axis for anvil (218) slides relative to lower jaw (216). Extensions (220) extend downwardly from anvil (218), distal of ramps (224, 226). Extensions (220) comprise ramped surfaces (222) that slope downwardly proximal of extensions (220). Extensions (220) may contact tissue during a procedure to prevent the tissue from being inserted too far within end effector (212) between jaws (216, 218), even when jaws (216, 218) are fully open. Extensions (220) may also provide consistent lateral alignment between anvil (218) and lower jaw (216) as anvil (218) is being closed toward lower jaw (216).

Figure 15:
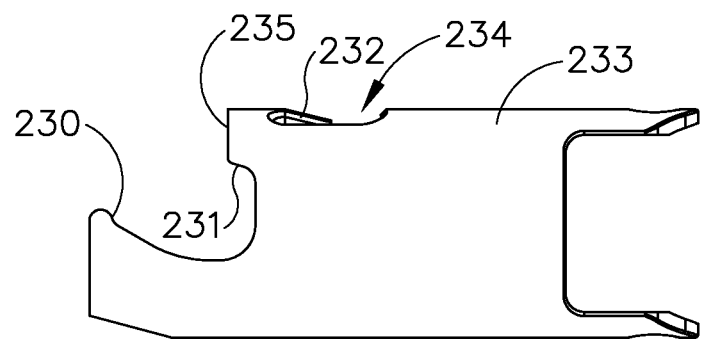
FIG. 15 depicts a side elevational view of a closure ring of the end effector of FIG. 12.
Figure 16:
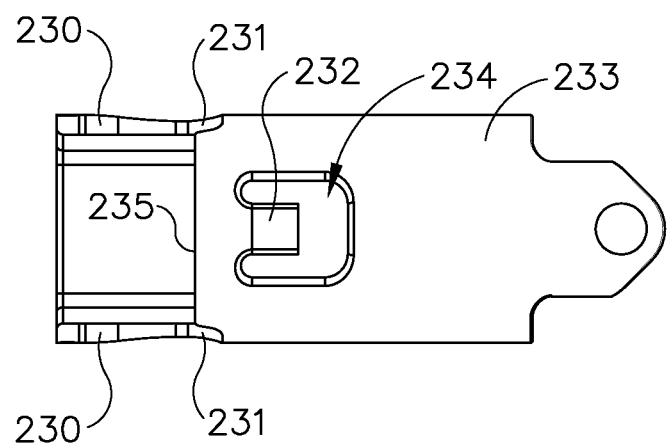
FIG. 16 depicts a top plan view of the closure ring of FIG. 15.

As shown in FIGS. 15-16, closure ring (233) comprises extensions (230), vertical surface (235), and tab (232). Tab (232) is positioned within a lateral hole or opening (234) that is formed through the sidewall of closure ring (233). Extensions (230) are positioned on the distal end of closure ring (233). Extensions (230) extend upwardly and slope downwardly in the proximal direction. Extensions (230) are shaped to correspond to ramped surfaces (222) of extensions (220) of anvil (218). Vertical surface (235) is positioned proximal of extensions (230) and is configured to engage vertical surface (228) of anvil (218). Vertical surface (235) extends around closure ring (233) and then proximally to form lower side surfaces (231). Side surfaces (231) slope downwardly in the proximal direction to correspond to upper side ramps (226) of anvil (218). Opening (234) is configured to receive tab (225) of anvil (218). Tab (232) of closure ring (233) extends proximally within opening (234) and slopes downwardly.

Figure 17A:
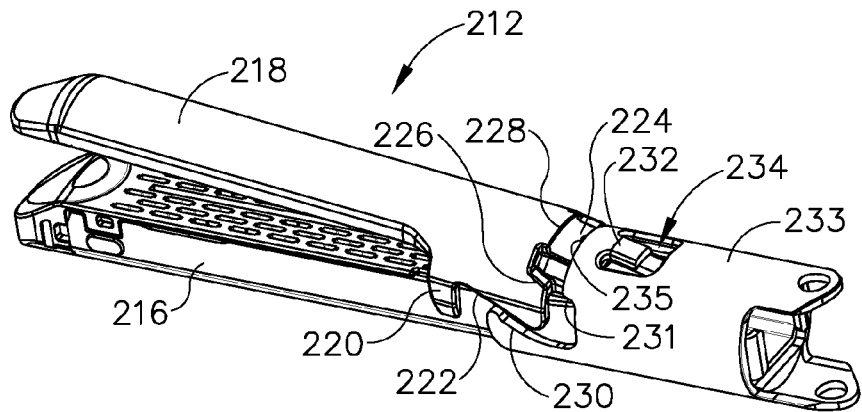
FIG. 17A depicts a perspective view of the end effector of FIG. 12 during a first instant of time during closure.
Figure 17B:
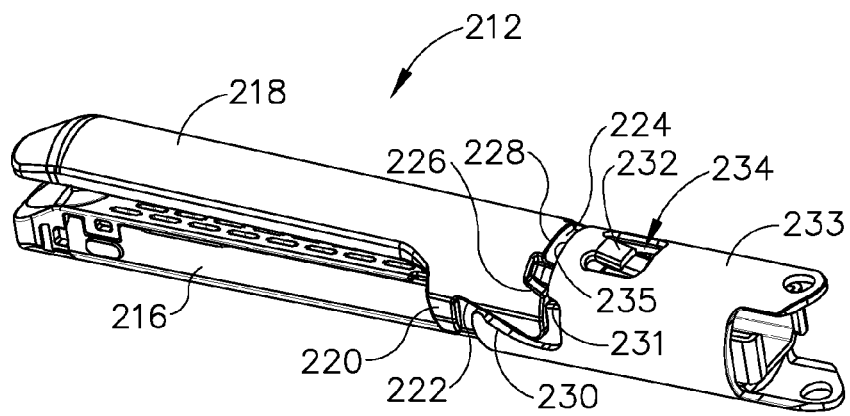
FIG. 17B depicts a perspective view of the end effector of FIG. 12 during a second instant of time during closure.
Figure 17C:
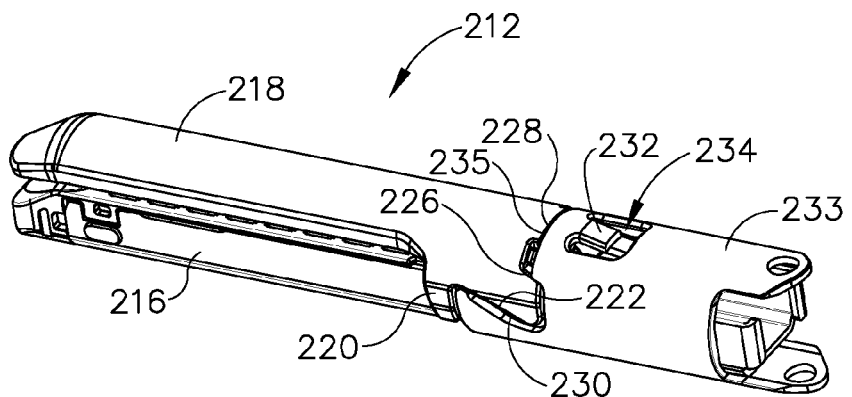
FIG. 17C depicts a perspective view of the end effector of FIG. 12 fully closed.

In an exemplary use, instrument (10) may be inserted to a surgical site in a nonarticulated state, with jaws (216, 218) closed. Once articulation joint (11) and end effector (212) are inserted to the desired site within the patient, anvil (218) may be pivoted away from lower jaw (216), as described below, to the open jaws (216, 218) to the position shown in FIG. 12 such that jaws (216, 218) may be positioned about tissue. Articulation joint (11) may be remotely articulated by articulation control (13), such that end effector (212) may be deflected to a desired angle (a). Alternatively, end effector (212) may be articulated at articulation joint (11) prior to opening jaws (216, 218). Closure trigger (26) may then be actuated toward pistol grip (24) to cause the closing of anvil (218) toward lower jaw (216), as shown in FIGS. 17A-17C. Such closing of anvil is provided through a closure tube (32) and closure ring (233), which both longitudinally translate relative to handle portion (20) and lower jaw (216) in response to pivoting of closure trigger (26) relative to pistol grip (24). Articulation joint (11) is operable to communicate longitudinal movement from closure tube (32) to closure ring (233).

As closure ring (233) translates distally in response to advancement of closure tube (32), closure ring (233) translates relative to anvil (218) to engage anvil (218). As shown in FIG. 17A, vertical surface (235) first engages central ramp (224) of anvil (218). As closure ring (233) translates distally, closure ring (233) cams along central ramp (224) of anvil (218) to pivot anvil (218) toward lower jaw (216). As closure ring (233) further translates distally, lower side surfaces (231) of closure ring (233) engage upper side ramps (226) of anvil (218), as shown in FIG. 17B. Once closure ring (233) engages side ramps (226), the mechanical load is transferred from central ramp (224) to side ramps (226). As closure ring (233) engages side ramps (226), closure ring (233) continues to pivot anvil (218) further closed toward lower jaw (216). FIG. 17C shows anvil (218) fully closed relative to lower jaw (216). At full closure, vertical surface (235) of closure ring (233) contacts vertical surface (228) of anvil (218). While much of the load is maintained on side ramps (226), some of the mechanical load may be maintained by or transferred to vertical surface (228). Closure ring (233) engages side ramps (226) and vertical surface (228) to close anvil (218) relative to lower jaw (216) and hold anvil (218) in position. It should be understood from the foregoing that several cam surfaces are used to close anvil (218) toward lower jaw (216). It should be understood that the above-described sequence takes advantage of surface interactions that are most efficient at compressing tissue during particular moments of time during the anvil (218) closure process.

Figure 18:
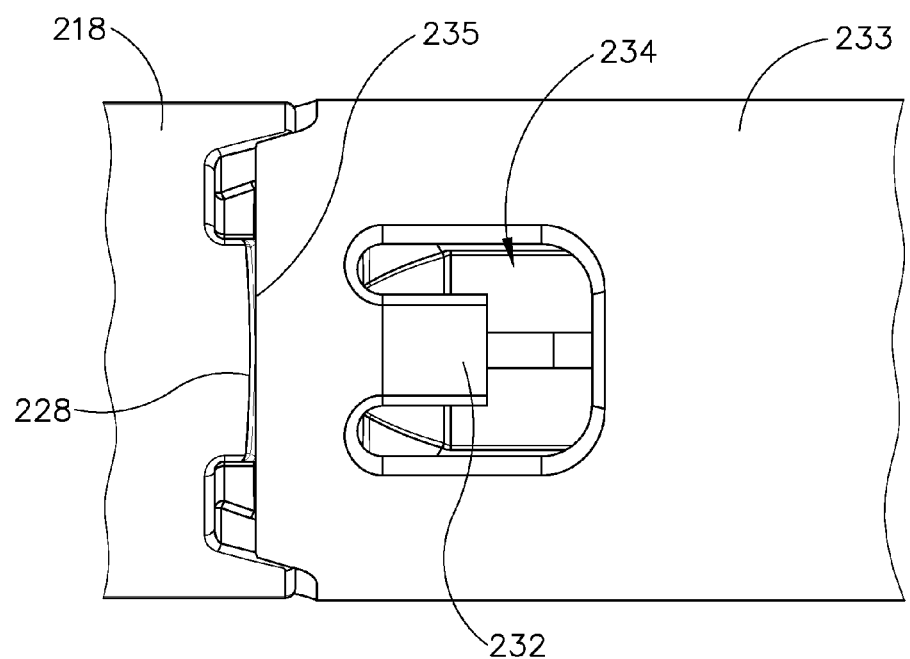
FIG. 18 depicts a partial top plan view of the end effector of FIG. 12, with the closure ring advanced to a distal position to close the pivoting jaw.

FIG. 18 shows anvil (218) and closure ring (233) in the fully closed position. Vertical surface (228) of anvil (218) contacts vertical surface (235) of closure ring (233). Vertical surface (228) has a curved profile, which concentrates the axial closure load at the center of vertical surface (235). In some instances, as anvil (218) closes relative to lower jaw (216), anvil (218) may slightly deflect laterally relative to closure ring (233). If anvil (218) is deflected laterally, the curved profile of vertical surface (228) transfers the load centrally to closure ring (233) regardless of the lateral deflection of anvil (218) and eventually corrects the deflection to properly align anvil (218). Also, by concentrating the load centrally, the tissue compression ability at the tip of anvil (218) is increased due to better mechanical advantage and better load transfer efficiency. Side ramps (226) also provide an overall load advantage that increases the available tissue compression ability at the tip of anvil (218). Once end effector (212) is closed, the tissue captured between anvil (218) and lower jaw (216) may be cut and stapled by actuating firing trigger (28) to drive firing beam (14).

Figure 19A:
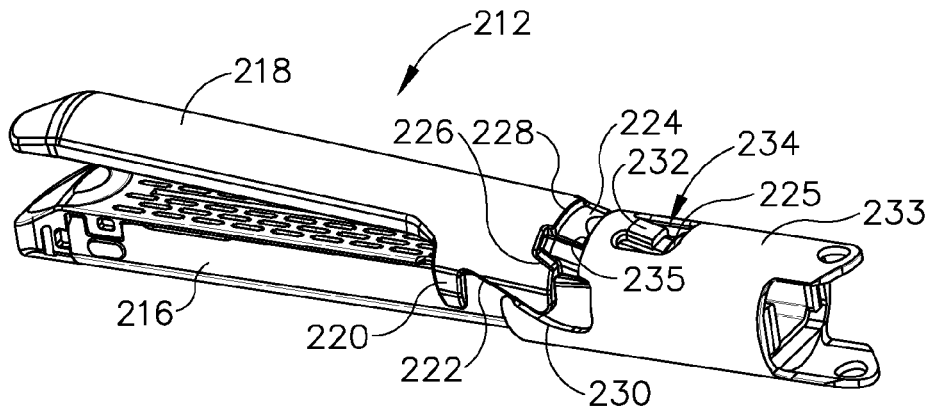
FIG. 19A depicts a perspective view of the end effector of FIG. 12 during a first instant of time during opening.
Figure 19B:
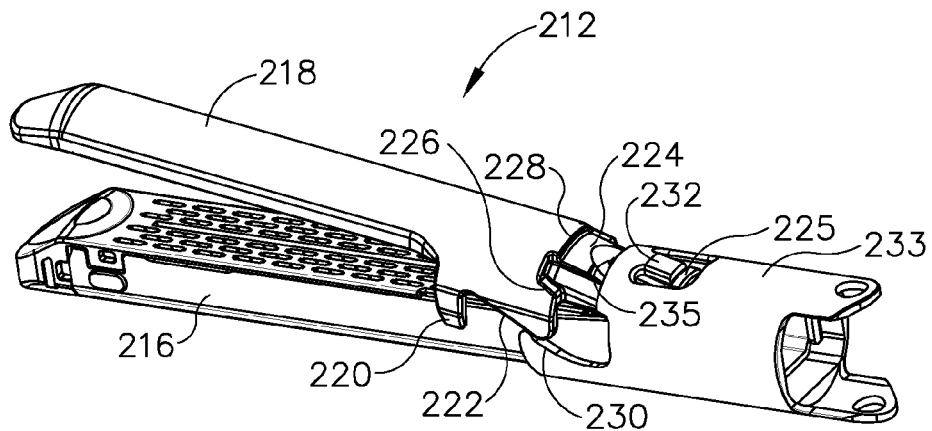
FIG. 19B depicts a perspective view of the end effector of FIG. 12 during a second instant of time during opening.
Figure 19C:
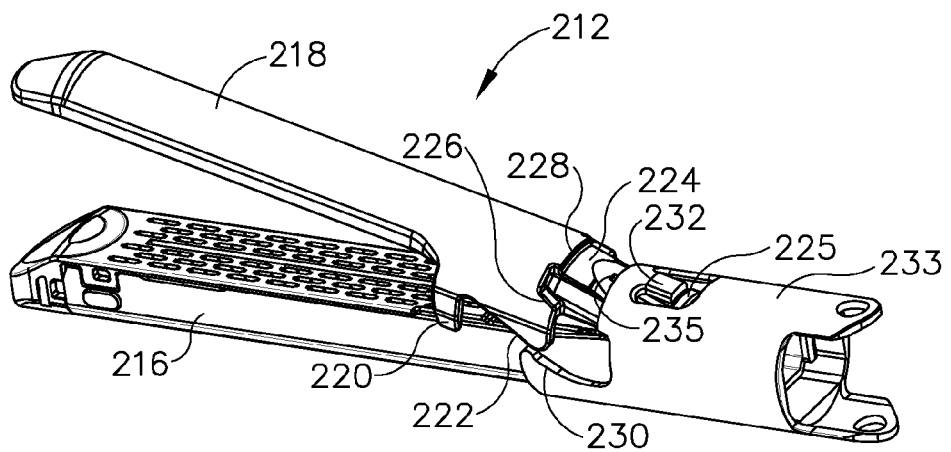
FIG. 19C depicts a perspective view of the end effector of FIG. 12 fully opened.

Once tissue positioned between jaws (216, 218) is cut and stapled, jaws (216, 218) may be opened to release the tissue, then end effector (212) may be pivoted back to the nonarticulated position by articulation control (13) and removed from the surgical site, with jaws (216, 218) closed. End effector (212) may then be opened to replace staple cartridge (37) with a new staple cartridge. To open end effector (212), closure trigger (26) may be released away from pistol grip (24) to cause closure ring (233) to translate proximally. As closure ring (233) translates proximally, closure ring (233) engages anvil (218) to pivot anvil (218) away from lower jaw (216), as shown in FIGS. 19A-19C. As closure ring (233) translates proximally, vertical surface (235) disengages from vertical surface (228) of anvil (218), as shown in FIG. 19A. Closure ring (233) also disengages from side ramps (226). Extensions (230) of closure ring (233) engage and cam along ramped surfaces (222) of anvil (218). This causes anvil (218) to pivot upwardly away from lower jaw (216). As shown in FIG. 19C, closure ring (233) continues to translate proximally to cause tab (232) of closure ring (233) to engage tab (225) of anvil (218). This causes anvil (218) to pivot to the fully open position. Staple cartridge (37) may be replaced with a new staple cartridge, and end effector (212) may be again inserted to the surgical site for further cutting and stapling.

B. Exemplary Channel Engagement Features

Figure 20:
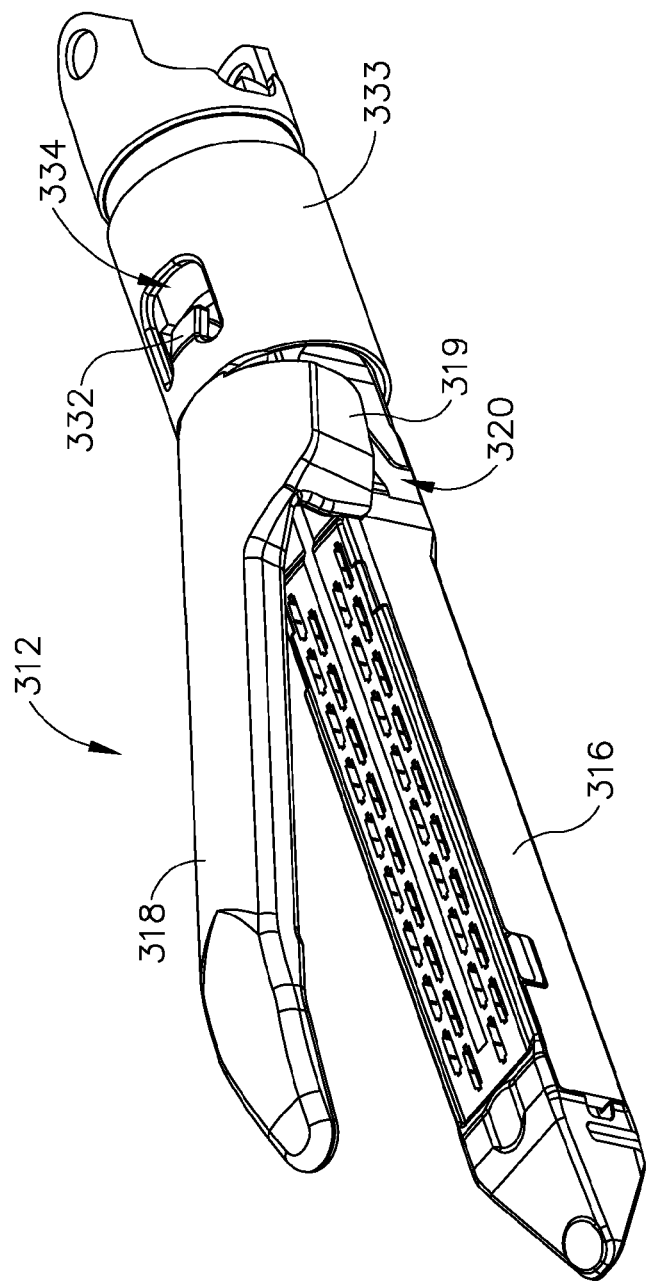
FIG. 20 depicts a perspective view of another exemplary end effector for use with the instrument of FIG. 1.
Figure 21:
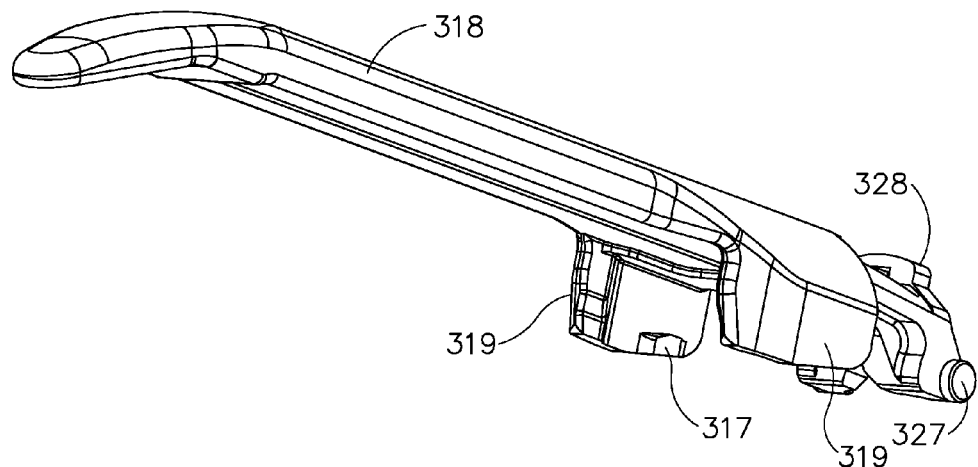
FIG. 21 depicts a perspective view of a pivoting jaw of the end effector of FIG. 20.
Figure 22:
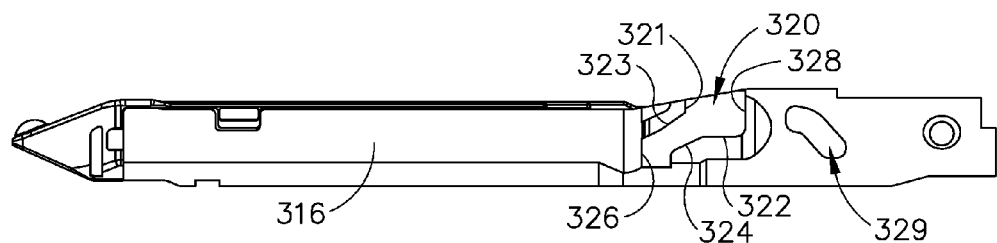
FIG. 22 depicts a side elevational view of a stationary lower jaw of the end effector of FIG. 20.

FIG. 20 shows another exemplary end effector (312) that may be readily incorporated into instrument (10). End effector (312) comprises a pivotable anvil (318), a lower jaw (316), and a closure ring (333). Pivotable anvil (318) is similar to pivotable anvil (18), except that pivotable anvil (318) comprises protrusions (317) extending inwardly from flanges (319), as shown in FIG. 21. The surfaces of protrusions (317) are ramped to aid protrusions (317) in camming against lower jaw (316). Lower jaw (316) is similar to lower jaw (16) of end effector (12), except that lower jaw (316) comprises a channel (320) on each outer face of lower jaw (316), as shown in FIG. 22. Channel (320) is sized to correspond to protrusions (317) of anvil (318). Channel (320) comprises a wide opening at the top of channel (320) that angles distally to a narrower opening at the bottom of channel (320). The distal edge of channel (320) comprises an upper vertical wall (321), a ramped wall (323) extending distally from vertical wall (321), and a lower vertical wall (326) extending downwardly from ramped wall (323). The proximal edge of channel (320) comprises a vertical wall (328) adjacent to a horizontal wall (322), and a ramped wall (324). Walls (321, 323) is configured to guide protrusions (317) through channel (320) as anvil (318) is translated relative to lower jaw (316), to thereby open and/or close anvil (318) relative to lower jaw (316). Lower jaw (316) comprises an opening (329) that receives pin (327) of anvil (318) such that anvil (318) is pivotable relative to lower jaw (316). Opening (329) is an elongate slot in this example. It should therefore be understood that pin (327) slides along opening (329) in addition to pivoting about its own axis within opening (329). This action may still be regarded as "pivoting" as defined herein, even though the pivot axis translates with pin (327) along opening (329) and is not in a fixed position. Closure ring (333) is similar to closure ring (33).

Figure 23A:
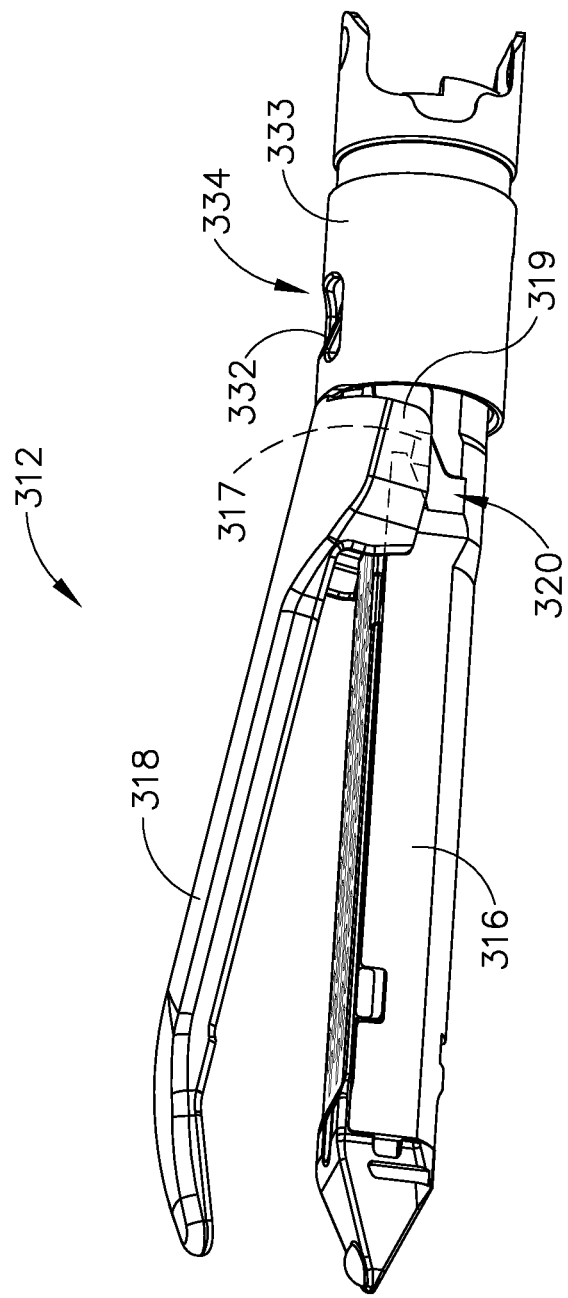
FIG. 23A depicts a perspective view of the end effector of FIG. 20 during a first instant of time during closure.
Figure 23B:
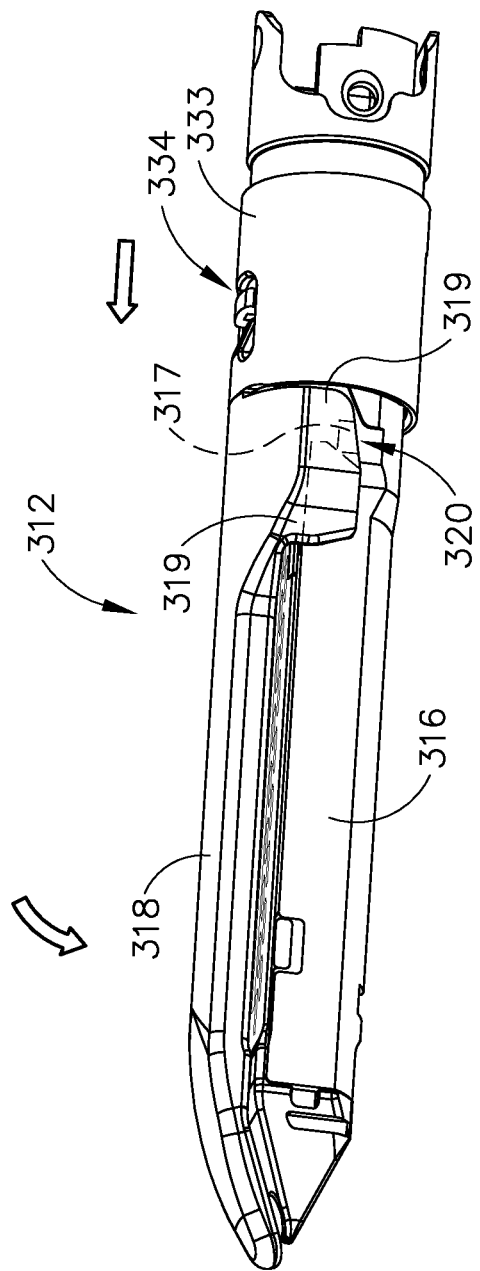
FIG. 23B depicts a perspective view of the end effector of FIG. 20 fully closed.

In an exemplary use, instrument (10) may be inserted to a surgical site in a nonarticulated state, with jaws (316, 318) closed. Once articulation joint (11) and end effector (312) are inserted to the desired site within the patient, jaws (316, 318) may be opened, as described below, and articulation joint (11) may be remotely articulated by an articulation control (13), such that end effector (312) may be deflected to a desired angle (α) to position tissue between jaws (316, 318). Alternatively, end effector (312) may be deflected at articulation joint (11) prior to opening jaws (316, 318). Closure trigger (26) may then be actuated toward pistol grip (24) to cause the closing of anvil (318) toward lower jaw (316), as shown in FIGS. 23A-23B. Such closing of anvil is provided through a closure tube (32) and closure ring (333), which both longitudinally translate relative to handle portion (20) and lower jaw (316) in response to pivoting of closure trigger (26) relative to pistol grip (24). Articulation joint (11) is operable to communicate longitudinal movement from closure tube (32) to closure ring (333).

As closure ring (333) translates distally in response to advancement of closure tube (32), closure ring (333) translates relative to anvil (318) to engage anvil (318). As shown in FIGS. 23A-23B, closure ring (333) engages anvil (318) to translate anvil (318) distally. As anvil (318) translates distally, protrusion (317) contacts ramped wall (323) of lower jaw (316). The ramped surfaces of protrusion (317) allow protrusion (317) to translate along ramped wall (323) of lower jaw (316). As anvil (318) continues to translate distally, ramped wall (323) cams against protrusion (317) to drive anvil (318) to pivot downwardly toward lower jaw (316). Near the end of the closure stroke, protrusions (317) of anvil (318) transition to shallower angled surfaces of ramped wall (323) and are cinched downwardly. Protrusions (317) and channel (320) are positioned distal to the pivot point of anvil (318) to increase the moment arm to close anvil (318). This improves load transfer to the distal end of anvil (318) to generate additional tissue compression ability. Once end effector (312) is closed, the tissue captured between anvil (318) and lower jaw (316) may be cut and stapled.

Figure 24A:
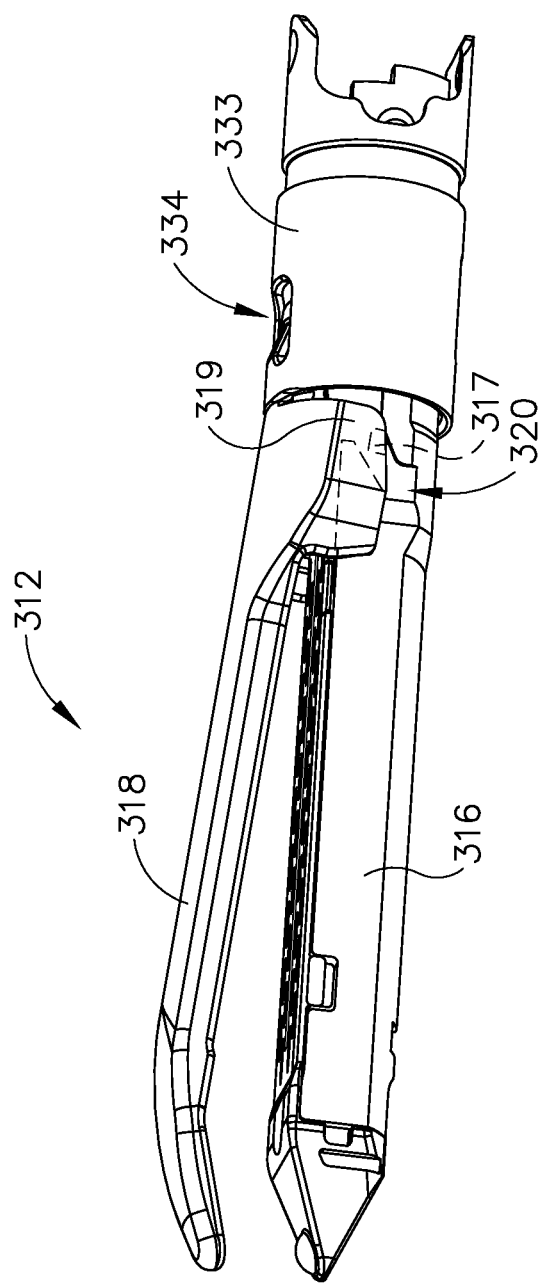
FIG. 24A depicts a perspective view of the end effector of FIG. 20 during a first instant of time during opening.
Figure 24B:
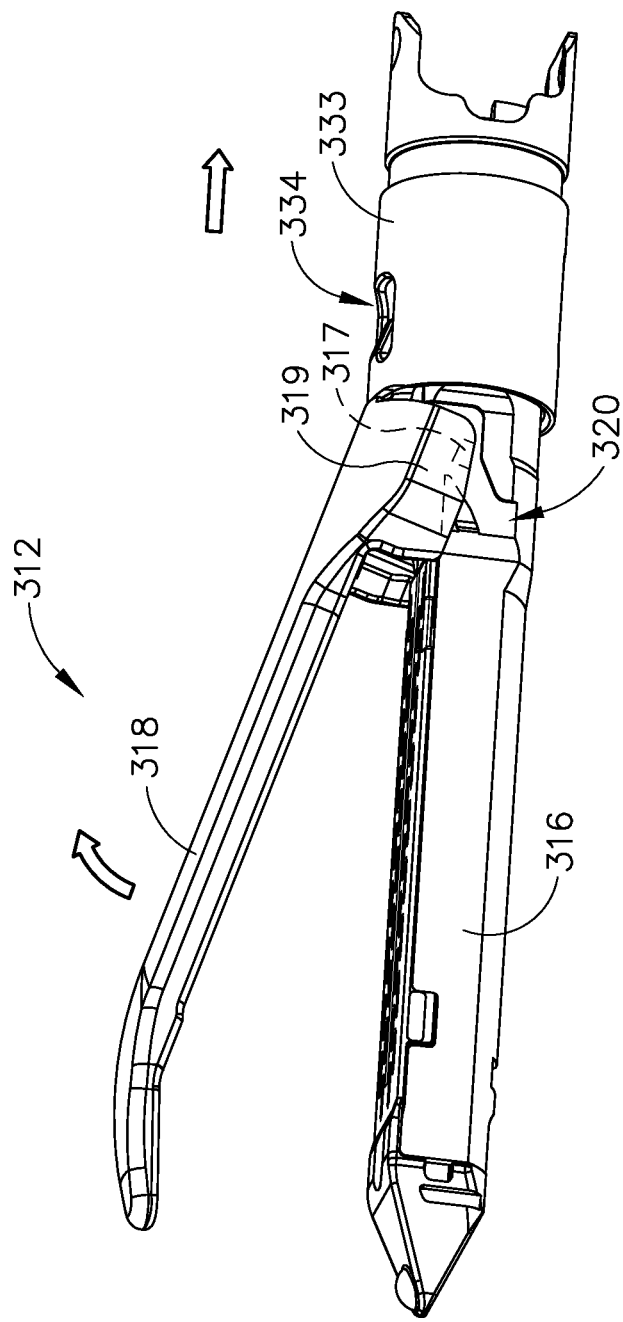
FIG. 24B depicts a perspective view of the end effector of FIG. 20 fully opened.

Once tissue positioned between jaws (316, 318) is cut and stapled, jaws (316, 318) may be opened to release the tissue, then end effector (312) may be pivoted back to the nonarticulated position by articulation control (13) and removed from the surgical site, with jaws (316, 318) closed. End effector (312) may then be opened to replace staple cartridge (37) with a new staple cartridge. To open end effector (312), closure trigger (26) may be released away from pistol grip (24) to cause closure ring (333) to translate proximally, as shown in FIGS. 24A-24B. As closure ring (333) translates proximally, closure ring (333) engages tab (328) of anvil (318) to pull anvil (318) proximally. As anvil (318) translates proximally, protrusions (317) disengage ramped wall (323) and anvil (318) pivots away from lower jaw (316) to an open position, as shown in FIG. 24B. Staple cartridge (37) may be replaced with a new staple cartridge, and end effector (312) may be again inserted to the surgical site for further cutting and stapling.

IV. Miscellaneous

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif. Similarly, those of ordinary skill in the art will recognize that various teachings herein may be readily combined with various teachings of any of the following: U.S. Pat. No. 5,792,135, entitled "Articulated Surgical Instrument For Performing Minimally Invasive Surgery With Enhanced Dexterity and Sensitivity," issued Aug. 11, 1998, the disclosure of which is incorporated by reference herein; U.S. Pat. No. 5,817,084, entitled "Remote Center Positioning Device with Flexible Drive," issued Oct. 6, 1998, the disclosure of which is incorporated by reference herein; U.S. Pat. No. 5,878,193, entitled "Automated Endoscope System for Optimal Positioning," issued Mar. 2, 1999, the disclosure of which is incorporated by reference herein; U.S. Pat. No. 6,231,565, entitled "Robotic Arm DLUS for Performing Surgical Tasks," issued May 15, 2001, the disclosure of which is incorporated by reference herein; U.S. Pat. No. 6,783,524, entitled "Robotic Surgical Tool with Ultrasound Cauterizing and Cutting Instrument," issued Aug. 31, 2004, the disclosure of which is incorporated by reference herein; U.S. Pat. No. 6,364,888, entitled "Alignment of Master and Slave in a Minimally Invasive Surgical Apparatus," issued Apr. 2, 2002, the disclosure of which is incorporated by reference herein; U.S. Pat. No. 7,524,320, entitled "Mechanical Actuator Interface System for Robotic Surgical Tools," issued Apr. 28, 2009, the disclosure of which is incorporated by reference herein; U.S. Pat. No. 7,691,098, entitled "Platform Link Wrist Mechanism," issued Apr. 6, 2010, the disclosure of which is incorporated by reference herein; U.S. Pat. No. 7,806,891, entitled "Repositioning and Reorientation of Master/Slave Relationship in Minimally Invasive Telesurgery," issued Oct. 5, 2010, the disclosure of which is incorporated by reference herein; U.S. Pub. No. 2013/0012957, entitled "Automated End Effector Component Reloading System for Use with a Robotic System, published Jan. 10, 2013, now U.S. Pat. No. 8,844,789, issued on Sep. 30, 2014, the disclosure of which is incorporated by reference herein; U.S. Pub. No. 2012/0199630, entitled "Robotically-Controlled Surgical Instrument with Force-Feedback Capabilities," published Aug. 9, 2012, now U.S. Pat. No. 8,820,605, issued on Sep. 2, 2014, the disclosure of which is incorporated by reference herein; U.S. Pub. No. 2012/0132450, entitled "Shiftable Drive Interface for Robotically-Controlled Surgical Tool," published May 31, 2012, now U.S. Pat. No. 8,616,431, issued on Dec. 31, 2013, the disclosure of which is incorporated by reference herein; U.S. Pub. No. 2012/0199633, entitled "Surgical Stapling Instruments with Cam-Driven Staple Deployment Arrangements," published Aug. 9, 2012, now U.S. Pat. No. 8,573,461, issued on Nov. 5, 2013, the disclosure of which is incorporated by reference herein; U.S. Pub. No. 2012/0199631, entitled "Robotically-Controlled Motorized Surgical End Effector System with Rotary Actuated Closure Systems Having Variable Actuation Speeds," published Aug. 9, 2012, now U.S. Pat. No. 8,602,288, issued on Dec. 20, 2013, the disclosure of which is incorporated by reference herein; U.S. Pub. No. 2012/0199632, entitled "Robotically-Controlled Surgical Instrument with Selectively Articulatable End Effector," published Aug. 9, 2012, now U.S. Pat. No. 9,301,759, issued on April 5, 2016, the disclosure of which is incorporated by reference herein; U.S. Pub. No. 2012/0203247, entitled "Robotically-Controlled Surgical End Effector System," published Aug. 9, 2012, now U.S. Pat. No. 8,783,541, issued on Jul. 22, 2014, the disclosure of which is incorporated by reference herein; U.S. Pub. No. 2012/0211546, entitled "Drive Interface for Operably Coupling a Manipulatable Surgical Tool to a Robot," published Aug. 23, 2012, now U.S. Pat. No. 8,479,969, issued on Jul. 9, 2013; U.S. Pub. No. 2012/0138660, entitled "Robotically-Controlled Cable-Based Surgical End Effectors," published Jun. 7, 2012, now U.S. Pat. No. 8,800,838, issued on Aug. 12, 2014, the disclosure of which is incorporated by reference herein; and/or U.S. Pub. No. 2012/0205421, entitled "Robotically-Controlled Surgical End Effector System with Rotary Actuated Closure Systems," published Aug. 16, 2012, now U.S. Pat. No. 8,573,465, issued on Nov. 5, 2013, the disclosure of which is incorporated by reference herein.

Versions of the devices described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:
1. An end effector for use with a surgical instrument, the end effector comprising:
    (a) a first jaw;
    (b) a second jaw pivotable relative to the first jaw, wherein the second jaw comprises a proximal end, wherein the proximal end comprises:

(i) a first engagement feature having a first ramped surface on a central portion of the proximal end of the second jaw,
(ii) a second engagement feature having a second ramped surface on at least one side portion of the proximal end of the second jaw, wherein the second engagement feature is distal to the first engagement feature, and
(iii) a third engagement feature, wherein the third engagement feature comprises a wall extending upwardly from a distal end of the first ramped surface; and
(c) a closure ring coupled with the second jaw, wherein the closure ring is translatable relative to the first jaw, wherein the closure ring is configured to first engage the first engagement feature and then engage the second engagement feature of the second jaw as the closure ring translates distally relative to the first jaw to thereby pivot the second jaw relative to the first jaw.

2. The end effector of claim 1, wherein the proximal end of the second jaw has a first side portion and a second side portion, wherein the second side portion is opposed to the first side portion, wherein the second ramped surface is positioned on the first side portion of the proximal end of the second jaw, wherein the second engagement feature further comprises a third ramped surface, wherein the third ramped surface is positioned on the second side portion of the proximal end of the second jaw.

3. The end effector of claim 1, wherein the closure ring is configured to transfer a mechanical load from the first engagement feature to the second engagement feature when the closure ring translates distally.

4. The end effector of claim 1, wherein the wall comprises a curved profile.

5. The end effector of claim 1, wherein a distal end of the closure ring comprises a wall, wherein the wall of the closure ring is configured to engage the third engagement feature of the second jaw after the closure ring has engaged the first engagement feature and the second engagement feature.

6. The end effector of claim 5, wherein the closure ring is configured to transfer a mechanical load from the second engagement feature to the third engagement feature when the closure ring translates distally.

7. The end effector of claim 1, wherein the second ramped surface slopes proximally downwardly.

8. The end effector of claim 7, wherein the closure ring comprises a protrusion, wherein the second jaw comprises a third ramped surface extending downwardly in a proximal direction, wherein the protrusion extends upwardly such that the protrusion is configured to engage the third ramped surface of the second jaw.

9. The end effector of claim 8, wherein the protrusion of the closure ring is configured to translate along the third ramped surface of the second jaw when the closure ring is translated from a distal position to a proximal position, wherein the closure ring is operable to pivot the second jaw away from the first jaw when the closure ring is translated from the distal position to the proximal position.

10. The end effector of claim 9, wherein the surgical instrument comprises a shaft, wherein the end effector is coupled to the shaft, wherein the shaft comprises an articulation feature operable to translate the end effector from a first position where the end effector and shaft are longitudinally aligned to a second position where a longitudinal axis of the end effector is obliquely oriented relative to a longitudinal axis of the shaft.

11. The end effector of claim 10, wherein the surgical instrument comprises a handle portion, wherein the handle portion is coupled to the shaft, wherein the handle portion comprises an actuator operable to translate the closure ring.

12. The end effector of claim 1, wherein the end effector is operable to staple tissue between the first and second jaws.

13. A method for closing an end effector, wherein the end effector comprises a first jaw, a second jaw pivotable relative to the first jaw, and a closure ring, wherein a proximal end of the second jaw comprises a first ramped surface and a second ramped surface, the method comprising the steps of:
(a) translating the closure ring relative to the first jaw in a distal direction such that the closure ring engages the first ramped surface to pivot the second jaw toward the first jaw;
(b) further translating the closure ring relative to the first jaw in the distal direction such that the closure ring engages the second ramped surface after the closure ring engages the first ramped surface, wherein the closure ring engaging the second ramp surface pivots the second jaw toward the first jaw, wherein the second ramped surface is laterally offset from the first ramped surface; and
(c) further translating the closure ring relative to the first jaw in the distal direction such that the closure ring engages a wall extending upwardly from the first ramped surface such that the closure ring maintains the second jaw in a closed position.

14. An end effector for use with a surgical instrument, the end effector comprising:
(a) a first jaw;
(b) a second jaw pivotable relative to the first jaw, wherein the second jaw comprises a proximal end, wherein the proximal end comprises:
(i) a central portion,
(ii) a first side portion,
(iii) a second side portion, wherein the second side portion is opposed to the first side portion,
(iv) a first engagement feature located on the central portion,
(v) a second engagement feature located on one or both of the first side portion and the second side portion, and
(vi) a third engagement feature located on the central portion distally relative to the first engagement feature, wherein the third engagement feature comprises a vertical wall having a curved profile located distally from the first engagement feature;
(c) a closure ring coupled with the second jaw, wherein the closure ring is translatable to the first jaw, wherein the closure ring is configured to translate a first range of motion and a second range of motion relative to the first jaw to thereby pivot the second jaw relative to the first jaw, wherein the closure ring is configured to engage the first engagement feature without engaging the second engagement feature while traveling the first range of motion, wherein the closure ring is configured to engage the second engagement feature while traveling the second range of motion; wherein the closure ring is configured to abut against the third engagement feature when the closure ring reaches the end of the second range of motion.

15. The end effector of claim 14, wherein the first engagement feature comprises a first sloped surface.

16. The end effector of claim 15, wherein the second engagement feature comprises a second sloped surface located on the first side portion and a third sloped surface located on the second side portion.

17. The end effector of claim 14, wherein the third engagement feature is configured to laterally align the second jaw relative to the first jaw.

\* \* \* \* \*